("12") United States Patent
Bodurka et al.

(10) Patent No.: US 10,716,474 B2
(45) Date of Patent: Jul. 21, 2020

(54) PATIENT SUPPORT APPARATUSES WITH LOCATION/MOVEMENT DETECTION

(71) Applicant: Stryker Corporation, Kalamazoo, MI (US)

(72) Inventors: Alexander Josef Bodurka, Schoolcraft, MI (US); Krishna Sandeep Bhimavarapu, Kalamazoo, MI (US); Jerald A. Trepanier, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/193,150

(22) Filed: Nov. 16, 2018

(65) Prior Publication Data
US 2019/0150737 A1 May 23, 2019

Related U.S. Application Data

(60) Provisional application No. 62/587,867, filed on Nov. 17, 2017.

(51) Int. Cl.
A61B 5/00 (2006.01)
H04L 12/26 (2006.01)
A61B 5/11 (2006.01)
A61G 7/018 (2006.01)
A61G 7/00 (2006.01)
(Continued)

(52) U.S. Cl.
CPC ............ A61B 5/002 (2013.01); A61B 5/1115 (2013.01); A61B 5/7465 (2013.01); A61G 7/00 (2013.01);
(Continued)

(58) Field of Classification Search
CPC ..... A61B 5/002; A61B 5/1115; A61B 5/7465; A61G 2203/30; A61G 2203/34;
(Continued)

(56) References Cited

U.S. PATENT DOCUMENTS 4,882,566 A 11/1989 Koerber, Sr. et al.
7,868,740 B2 * 1/2011 McNeely ............... A61G 12/00
340/286.07

(Continued)

FOREIGN PATENT DOCUMENTS

EP 1623666 A2 8/2005
WO 2008098346 A1 8/2008

Primary Examiner — Quan-Zhen Wang
Assistant Examiner — Rajsheed O Black-Childress
(74) Attorney, Agent, or Firm — Warner Norcross + Judd LLP

(57) ABSTRACT

A patient support apparatus includes a first transceiver adapted to wirelessly communicate with a second transceiver of a headwall interface that is positioned off of the patient support apparatus. A communication link is automatically established between the first and second transceivers without requiring a user of the patient support apparatus to activate a designated control and without requiring the user to identify the headwall interface. The first transceiver includes a unique identifier assigned to the headwall interface in its messages to the headwall interface. The first transceiver may also automatically transmit a disconnect signal to the headwall interface indicating the termination of the communication link is not accidental. The disconnect signal is sent based on one or more of the following: (1) a brake being off, (2) an A/C power cord being unplugged; and/or (3) a signal strength between the transceivers decreasing.

20 Claims, 11 Drawing Sheets

(51) Int. Cl.
    *A61G 7/015* (2006.01)
    *A61G 7/005* (2006.01)
    *A61G 7/012* (2006.01)

(52) U.S. Cl.
    CPC .............. *A61G 7/018* (2013.01); *H04L 43/10*
        (2013.01); *A61G 7/005* (2013.01); *A61G 7/012*
        (2013.01); *A61G 7/015* (2013.01); *A61G*
        *2203/30* (2013.01); *A61G 2203/34* (2013.01);
        *A61G 2203/36* (2013.01)

(58) Field of Classification Search
    CPC ...... A61G 2203/36; A61G 7/00; A61G 7/005;
        A61G 7/012; A61G 7/015; A61G 7/018;
        H04L 43/10
    See application file for complete search history.

(56) References Cited

U.S. PATENT DOCUMENTS

| | | | |
|---|---|---|---|
| 8,125,318 | B2 | 2/2012 | Heimbrock et al. |
| 8,169,304 | B2 | 5/2012 | Schuman, Sr. et al. |
| 8,272,892 | B2 | 9/2012 | McNeely et al. |
| 8,319,633 | B2 | 11/2012 | Becker et al. |
| 8,334,777 | B2 | 12/2012 | Wilson et al. |
| 8,384,526 | B2 | 2/2013 | Schuman |
| 8,392,747 | B2 | 5/2013 | Ferguson et al. |
| 8,461,968 | B2 | 6/2013 | Ball et al. |
| 8,756,078 | B2 | 6/2014 | Collins, Jr. et al. |
| 9,999,375 | B2 | 6/2018 | Hayes et al. |
| 2007/0150554 | A1 | 6/2007 | Simister |
| 2007/0210917 | A1 | 9/2007 | Collins, Jr. et al. |
| 2013/0048705 | A1* | 2/2013 | Tallent .................. G06Q 10/06 235/375 |
| 2013/0091631 | A1 | 4/2013 | Hayes et al. |
| 2014/0297327 | A1 | 10/2014 | Heil et al. |
| 2015/0033295 | A1 | 1/2015 | Huster |
| 2015/0081335 | A1* | 3/2015 | Dixon .................. G06Q 50/22 705/3 |
| 2015/0128346 | A1 | 5/2015 | Hollyoak et al. |
| 2015/0231006 | A1 | 8/2015 | Bhimavarapu et al. |
| 2016/0038361 | A1 | 2/2016 | Bhimavarapu et al. |
| 2016/0296143 | A1* | 10/2016 | Hayes .................. A61B 5/6892 |
| 2018/0296415 | A1* | 10/2018 | Seim .................. A61G 7/0524 |

* cited by examiner

PATIENT SUPPORT APPARATUSES WITH LOCATION/MOVEMENT DETECTION

CROSS-REFERENCE TO RELATED APPLICATIONS

This application claims priority to commonly assigned U.S. provisional patent application Ser. No. 62/587,867 filed Nov. 17, 2017, by inventors Alexander Josef Bodurka et al. and entitled PATIENT SUPPORT APPARATUSES WITH LOCATION/MOVEMENT DETECTION, the complete disclosure of which is incorporated herein by reference.

BACKGROUND

The present disclosure relates to medical facilities having headwalls with one or more connectors that enable communication between a patient support apparatus (e.g. a bed, stretcher, cot, recliner, wheelchair, etc.) and one or more devices that are coupled to a headwall communication interface (e.g. a nurse call system, entertainment controls, room controls, etc.).

Medical facilities, such as hospitals, typically include a headwall having one or more outlets and/or other types of connectors into which the plugs of cables connected to medical devices can be inserted. For example, headwalls will typically include at least one outlet that interfaces with a nurse-call system and which is designed to accept a cable from a hospital bed, or from a hand-held pendant positioned on the bed. When the cable is plugged into this outlet, a patient positioned on the bed is able to press a button to summon a nurse and/or to communicate aurally with the nurse.

Existing headwall connectors also typically communicate with one or more environmental controls, such as one or more controls for in-room televisions, room lights, and/or electrically movable curtains. When the appropriate device and its associated cable are plugged into the headwall connector from a bed, pendant, or other device, a person is able to control the environmental control via the device (e.g. bed, pendant, or other device). Thus, for example, a patient positioned on a bed is able to control the volume of a television in the room via controls on the bed due to the proper cable being connected from the bed to the headwall. In some instances, a single cable is plugged into a single connector on the headwall and used for communicating both with the nurse call system of the medical facility, and for communicating with the one or more environmental controls. In such instances, the headwall connector is coupled to a room interface board that forwards the environmental control signals to the appropriate environmental control unit, and forwards the nurse call signals to the appropriate component of the nurse call system.

SUMMARY

A patient support apparatus is provided that includes circuitry for wirelessly detecting a location and/or movement of the patient support apparatus utilizing communications with a headwall interface of a medical facility. In some embodiments, the wireless circuitry automatically determines whether the patient support apparatus is entering a room or exiting a room. One or more steps may automatically be taken in response to such a determination, such as, but not limited to, changing a setting on one or more non-patient support apparatus devices (e.g. a television, a radio, a thermostat, a room light, etc.). In other embodiments, the circuitry confirms the location of the patient support apparatus to a specific room and/or a specific zone within a room. One or more reminders may also be provided to the caregiver in response to the detection of movement of the patient support apparatus.

According to one embodiment of the present disclosure, a patient support apparatus is provided that includes a support surface, a first transceiver, a second transceiver, and a controller. The support surface is adapted to support a person thereon. The first transceiver is adapted to establish first wireless communication with a first headwall unit positioned on a headwall of a room, and the second transceiver is adapted to establish second wireless communication with a second headwall unit positioned in the room. The controller automatically determines from the first and second wireless communications at least one of the following: (1) when the patient support apparatus is leaving the room, and (2) when the patient support apparatus is entering the room.

According to other aspects of the present disclosure, the controller automatically determines when the patient support apparatus is leaving the room, and the controller does so by monitoring an order in which the first and second transceivers discontinue communication with the first and second headwall units, respectively.

In some embodiments, the controller automatically determines when the patient support apparatus is entering the room, and the controller does so by monitoring an order in which the first and second transceivers establish communication with the first and second headwall units, respectively.

The first transceiver may be an infrared transceiver or an optical transceiver, and the second transceiver may be a radio frequency transceiver, such as, but not limited to, a Bluetooth transceiver.

The first transceiver communicates first periodic heartbeat messages with the first headwall unit and the second transceiver communicates second periodic heartbeat messages with the second headwall unit, in some embodiments. The controller forwards information to a remote device, such as, but not limited to, a server, indicative of successful communication of the first and second heartbeat messages. In some embodiments, the information indicative of successful communication is forwarded to the remote device using a third transceiver.

The patient support apparatus may also include a nurse call cable interface and a nurse call connection detector. The nurse call cable interface allows a nurse call cable to be connected between the patient support apparatus and a nurse call outlet of a nurse call system. The nurse call connection detector detects when the nurse call cable is in communication with the nurse call system. The controller is further adapted to remind the caregiver to couple the nurse call cable between the patient support apparatus and the nurse call outlet if the caregiver fails to do so and if the first and second transceivers have established communication with the first and second headwall units, respectively.

In some embodiments, the patient support apparatus also includes a patient presence detector adapted to detect when a patient is present on the support surface and when a patient is not present on the support surface. In such embodiments, the controller may further be adapted to automatically deactivate at least one function of the patient support apparatus if the controller determines the patient support apparatus is leaving the room and the patient is not present on the support surface.

The controller, in some embodiments, automatically sends a message to a remote device in response to determining the patient support apparatus is leaving the room. The message may include an instruction to perform at least one of the following: (1) turn off a room light; (2) turn off a radio; (3) turn off a television; and (4) change a temperature setting in the room. Other instructions and/or actions may also or alternatively be taken.

According to another embodiment of the present disclosure, a patient support apparatus is provided that includes a support surface, a first transceiver, a second transceiver, and a controller. The support surface is adapted to support a person thereon. The first transceiver is adapted to establish first wireless communication with a first headwall unit positioned on a headwall of a room, and the second transceiver is adapted to establish second wireless communication with a second headwall unit positioned in the room. The controller automatically sends a first message to a remote device indicating the patient support apparatus is not in the room if the first and second transceivers are unable to establish the first and second wireless communication with the first and second headwall units, respectively.

According to other aspects, the controller is further adapted to send a second message to the remote device indicating the patient support apparatus is in a particular bay of the room if the first and second transceivers are able to establish first and second wireless communication with the first and second headwall units, respectively.

In some embodiments, the controller sends a third message to the remote device indicating the patient support apparatus is in the room and an error condition exists if only one of the first and second transceivers is able to establish communication with the first and second headwall units, respectively.

The controller may further be adapted to automatically determine from the first and second wireless communications at least one of the following: (1) when the patient support apparatus is leaving the room, and (2) when the patient support apparatus is entering the room.

When leaving the room, the controller may be adapted to automatically deactivate at least one function of the patient support apparatus if the controller determines the patient is not present on the support surface. Additionally, or alternatively, the controller may also send a message to a remote device in response to determining the patient support apparatus is leaving the room, and the message may include an instruction to perform at least one of the following: (1) turn off a room light; (2) turn off a radio; (3) turn off a television; and (4) change a temperature setting in the room.

When entering the room, the controller may be adapted to automatically activate at least one function of the patient support apparatus. Additionally or alternatively, the controller may be further adapted to send a message to a remote device in response to determining the patient support apparatus is entering the room. The message may include an instruction to perform at least one of the following: (1) turn on a room light; (2) turn on a radio; (3) turn on a television; (4) change a temperature setting in the room; and (5) alert a caregiver to couple a nurse call cable between the patient support apparatus and a nurse call interface of a nurse call system.

According to another aspect of the present disclosure, a patient support apparatus is provided that includes a support surface, a movement detector, and a controller. The support surface is adapted to support a person thereon. The movement detector detects if the patient support apparatus is moving into or out of a room. The controller automatically performs a first action if the movement detector detects the patient support apparatus is moving out of the room and automatically performs a second action if the movement detector detects the patient support apparatus is moving into the room.

The movement detector, in some embodiments, includes a first transceiver adapted to establish first wireless communication with a first headwall unit positioned on a headwall of the room and a second transceiver adapted to establish second wireless communication with a second headwall unit positioned in the room. Movement into and out of the room is established by monitoring an order in which the first and second transceivers establish or discontinue communication with the first and second headwall units, respectively.

In any of the embodiments, the patient support apparatus may be a bed, recliner, cot, stretcher, wheelchair, or other type of mobile structure adapted to support a patient.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
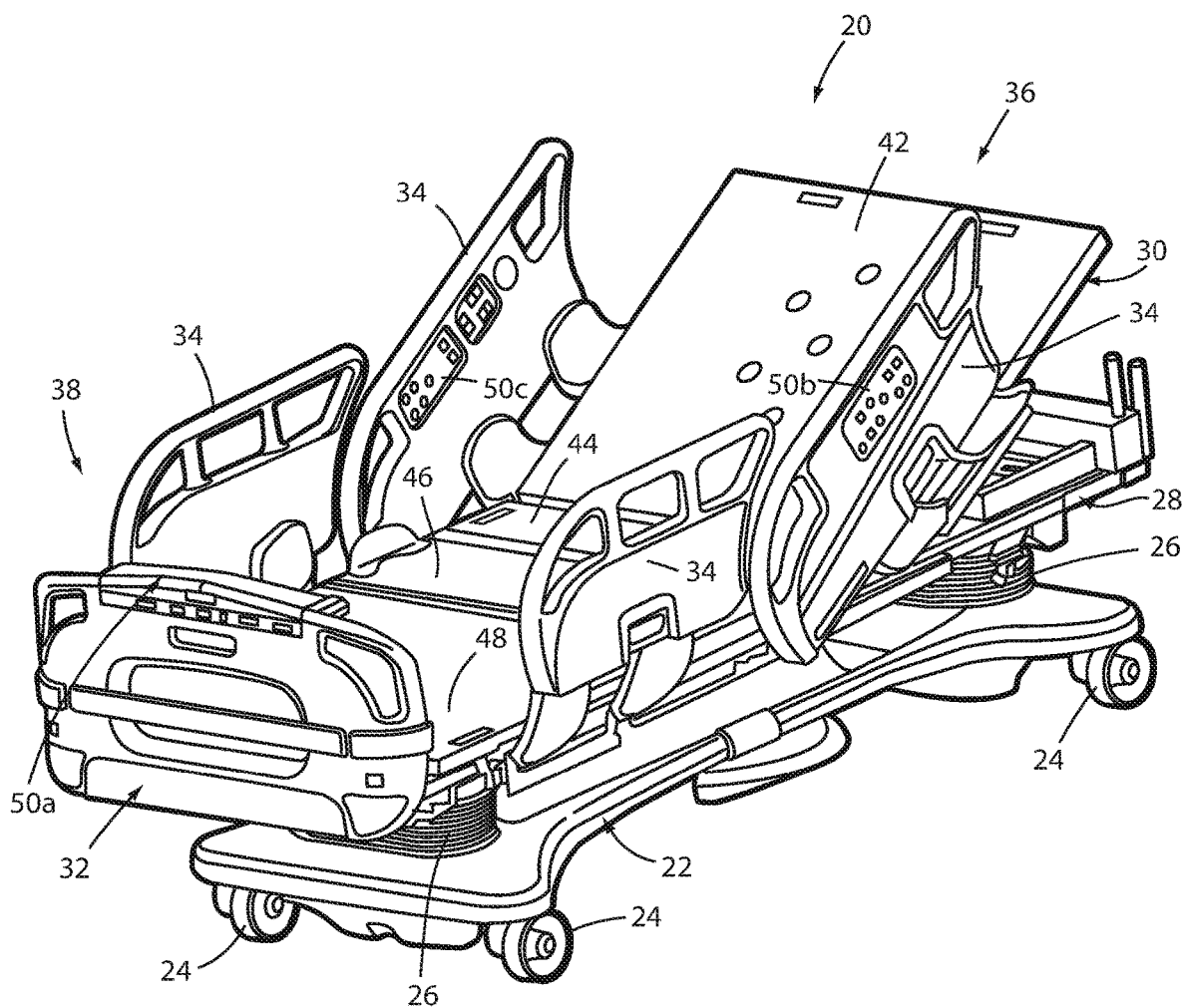
FIG. 1 is a perspective view of a patient support apparatus according to a first embodiment of the disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, or any other mobile structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 (which may be removable) and a plurality of siderails 34. Siderails 34 are all shown in a raised position in FIG. 1 but are each individually movable to a lower position in which ingress into, and egress out of, patient support apparatus 20 is not obstructed by the lowered siderails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when a person lies thereon, his or her head will be positioned adjacent head end 36 and his or her feet will be positioned adjacent foot end 38.

Litter frame 28 provides a structure for supporting support deck 30, footboard 32, and siderails 34. Support deck 30 provides a support surface for a mattress 40 (FIG. 2), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the patient. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Patient support apparatus 20 further includes a plurality of user interfaces 50 that enable a user of patient support apparatus 20, such as a patient and/or an associated caregiver, to control one or more aspects of patient support apparatus 20. In the embodiment shown in FIG. 1, patient support apparatus 20 includes a footboard user interface 50a, a pair of outer siderail user interfaces 50b (only one of which is visible), and a pair of inner siderail user interfaces 50c (only one of which is visible). Footboard user interface 50a and outer siderail user interfaces 50b are intended to be used by caregivers, or other authorized personnel, while inner siderail user interfaces 50c are intended to be used by the patient associated with patient support apparatus 20. Not all of the user interfaces 50 include the same controls and/or functionality. In the illustrated embodiment, footboard user interface 50a includes a complete set of controls for controlling patient support apparatus 20 while user interfaces 50b and 50c include a selected subset of those controls.

The controls of user interfaces 50 allow a user to control one or more of the following: change a height of support deck 30, raise or lower head section 42, activate and deactivate a brake for wheels 24, arm and disarm an exit detection system and, as will be explained in greater detail below, communicate with the particular IT infrastructure installed in the healthcare facility in which patient support apparatus 20 is positioned. Inner siderail user interfaces 50c may also include a nurse call control that enables a patient to call a nurse. A speaker and microphone are included in order to allow the patient to aurally communicate with the remotely positioned nurse.

Footboard user interface 50a is implemented in the embodiment shown in FIG. 1 as a control panel having a lid (flipped down in FIG. 1) underneath which is positioned a plurality of controls. The controls may be implemented as buttons, dials, switches, or other devices. Any of user interfaces 50a-c may also include a display for displaying information regarding patient support apparatus 20. The display may be a touchscreen in some embodiments.

The mechanical construction of patient support apparatus 20, as shown in FIG. 1, is the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. The construction of patient support apparatus 20 may take on a wide variety of different forms. In some embodiments, other than the components described below, patient support apparatus 20 is constructed in any of the manners described in commonly assigned, U.S. Pat. No. 8,689,376 issued Apr. 8, 2014 by inventors David Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is hereby incorporated herein by reference. In other embodiments, those components of patient support apparatus 20 not described below are constructed in any of the manners described in commonly assigned, U.S. patent application Ser. No. 13/775,285 filed Feb. 25, 2013 by inventors Guy Lemire et al. and entitled HOSPITAL BED, the complete disclosure of which is also hereby incorporated herein by reference. In still other embodiments, those components of patient support apparatus 20 not described below are constructed in any of the manners disclosed in commonly assigned, U.S. patent application Ser. No. 14/212,009 filed Mar. 14, 2014 by inventors Christopher Hough et al., and entitled MEDICAL SUPPORT APPARATUS. The mechanical construction of patient support apparatus 20 may also take on forms different from what is disclosed in the aforementioned references.

Figure 2:
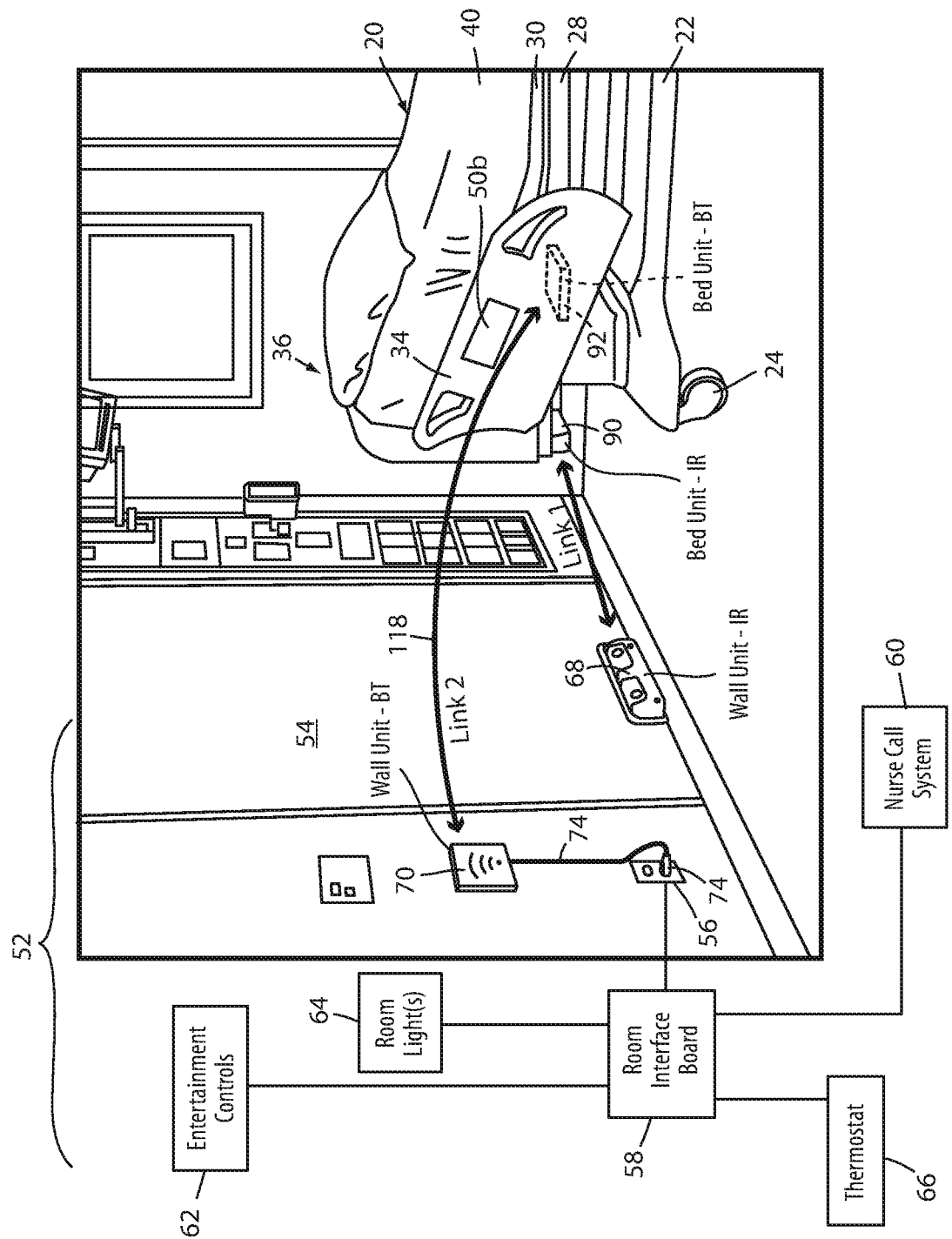
FIG. 2 is a perspective view of the patient support apparatus of FIG. 1 shown in a hospital room adjacent a headwall having a headwall interface.

FIG. 2 illustrates patient support apparatus 20 coupled to the IT infrastructure 52 of an illustrative healthcare facility according to one common configuration. As shown therein, the healthcare facility includes a headwall 54, a cable interface 56 mounted to the headwall 54, a room interface board 58 in communication with cable interface 56, and a plurality devices and components in communication with the room interface board 58, such as a nurse call system 60, a set of entertainment controls 62, one or more room lights 64, and a thermostat 66. Cable interface 56, room interface board 58, nurse call system 60, entertainment controls 62, room lights 64, and thermostat 66 may all be conventional pre-existing components that are installed in the healthcare facility independently of patient support apparatus 20 and its associated headwall interfaces 72, as will be discussed in more detail below. Additional IT infrastructure beyond what is shown in FIG. 2 may also be present in the healthcare facility, some examples of which are discussed in more detail below with respect to FIG. 5.

Entertainment controls 62 are conventional controls that control one or more aspects of the entertainment equipment that may be present in the particular room in which patient support apparatus 20 is located. Such entertainment equipment may include a television, video recorder, radio, etc., and entertainment controls 62 may include controls for controlling the volume, the channel, and the power. Room lights 64 provide lighting to one or more sections of the room in which patient support apparatus 20 is located. Room lights 64 may be conventional overhead lights and/or one or more night lights or other more localized lights within the room. Thermostat 66 controls the temperature of the room and/or a portion of the room (e.g. a particular bay) in which patient support apparatus 20 is located. Thermostat 66 is in communication with a conventional Heating, Ventilation, and Air Conditioning (HVAC) system. Nurse call system 60 may be a conventional nurse call system having one or more nurses' stations positioned throughout the healthcare facility. Nurse call system 60 routes room calls from patient support apparatus 20 to one or more nurses' stations so that the patient is able to speak with a remotely positioned nurse at a nurses' station while the patient is supported on patient support apparatus 20, as is known in the art.

Figure 4:
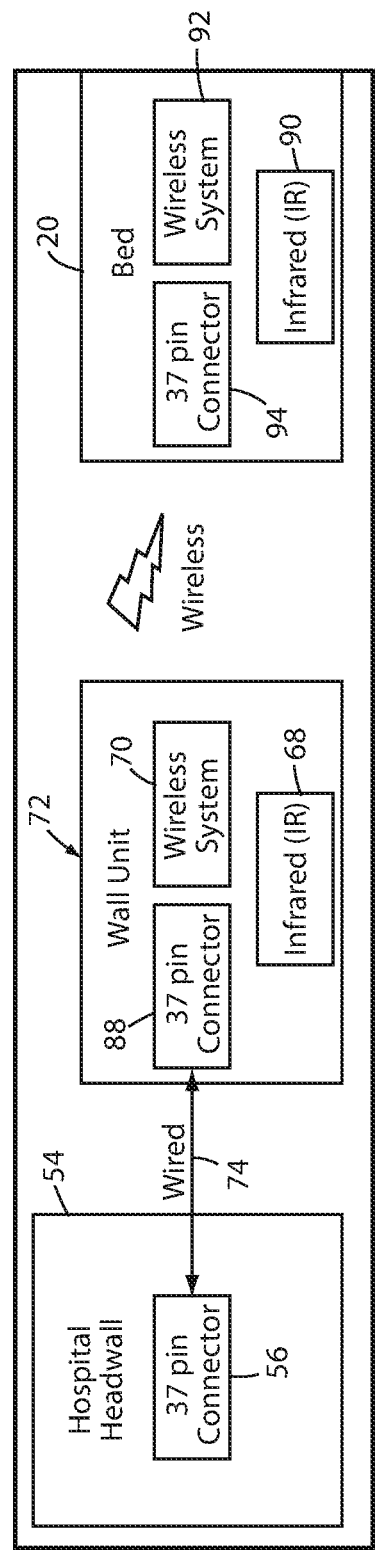
FIG. 4 is a block diagram of an alternative headwall interface.

Patient support apparatus 20 is adapted to wirelessly communicate with a first wall unit 68 and a second wall unit 70. First and second wall units 68 and 70 together form a headwall interface 72. In the embodiment shown in FIG. 1, first and second wall units 68 and 70 are two separate wall units. In other embodiments, such as shown in FIG. 4, wall units 68 and 70 are combined into a single wall unit, as discussed in more detail below. Regardless of whether coupled together in a single housing or separated into two physically disparate units, first and second wall units 68 and 70 are adapted to communicate with each other, in at least some embodiments. Such communication takes place via a wired connection when units 68 and 70 are combined in a single housing, and may take place wirelessly when units 68 and 70 are physically separated. In still other embodiments, units 68 and 70 are not adapted to communicate with each other.

Second wall unit 70 includes a cable 74 that is coupled to cable interface 56. Cable 74 allows second wall unit 70 to communicate with cable interface 56 and all of the components in communication with cable interface 56 (e.g. nurse call system 60, room interface board 58, etc.). Cable 74 includes a connector 76 (FIG. 3) that is adapted to mate with cable interface 56.

Figure 3:
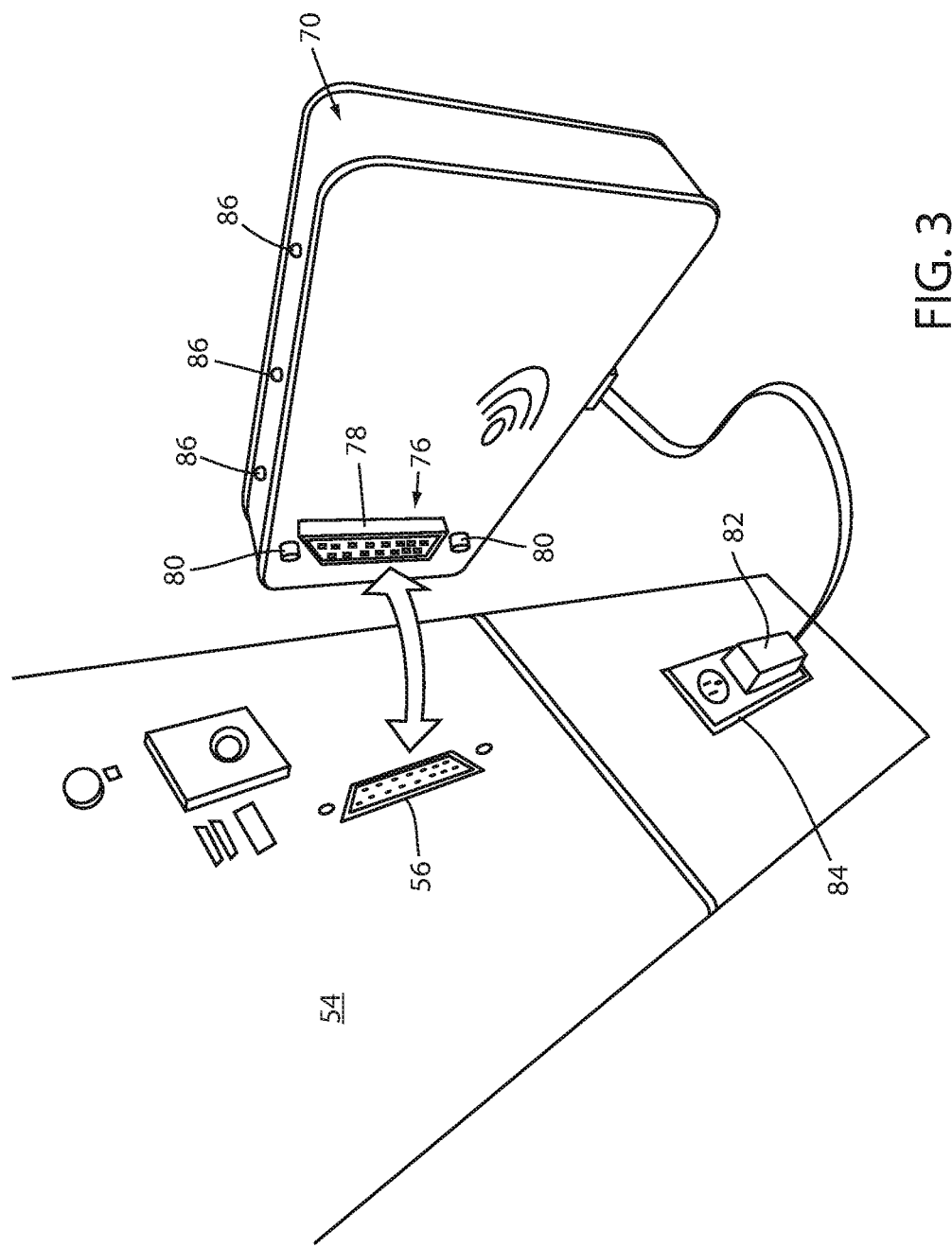
FIG. 3 is perspective view of an embodiment of one of the wall units of the headwall interface of FIG. 2.

FIG. 3 illustrates an alternative embodiment of second wall unit 70 in which cable 74 has been omitted. In this embodiment, second wall unit 70 has connector 76 integrated therein and second wall unit 70 couples directly to cable interface 56. Connector 76 in this embodiment includes an integral plug 78 that is adapted to be inserted into cable interface 56, which is a conventional cable interface that exists within a medical facility. Cable interface 56 is a receptacle that is dimensioned and shaped to selectively frictionally retain plug 78 therein and to support the entire second wall unit 70. One or more alignment posts 80 may be included with plug 78 in order to more securely retain second wall unit 70 to cable interface 56, if desired.

In the embodiment shown in FIG. 3, plug 78 is a 37 pin connector that includes 37 pins adapted to be inserted into 37 mating sockets of cable interface 56. Such 37 pin connections are one of the most common types of connectors found on existing headwalls of medical facilities for making connections to the nurse call system 60 and/or the room interface board 58. Second wall unit 70 of FIGS. 2 and 3 is therefore configured to mate with one of the most common type of cable interfaces 56 used in medical facilities. Such 37 pin connectors, however, are not the only type of connectors, and it will be understood that second wall unit 70 and cable 74 can be adapted to electrically couple to different types of cable interfaces 56. One example of such an alternative cable interface 56 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of cable interface 56 and corresponding cable connectors 76 may be utilized.

In the embodiment shown in FIG. 3, second wall unit 70 includes an electrical plug 82 adapted to be inserted into a conventional electrical outlet 84. Electrical plug 82 enables second wall unit 70 to receive power from the mains electrical supply via outlet 84. It will be appreciated that, in some embodiments, second wall unit 70 is battery operated and plug 82 may be omitted. In still other embodiments, second wall unit 70 may be both battery operated and include plug 82 so that, in the event of a power failure, battery power supplies power to second wall unit 70, and/or in the event of a battery failure, electrical power is received through outlet 84.

The embodiment of second wall unit 70 shown in FIG. 3 also includes a plurality of status lights 86. Status lights 86 provide visual indications about one or more aspects of second wall unit 70. For example, in some embodiments, the illumination of one of status lights 86 indicates that second wall unit 70 is in successful communication with room interface board 58. The illumination of another one of status lights 86 may indicate that second wall unit 70 is in successful communication with patient support apparatus 20. Still further, the illumination of one or more additional status lights 86 may indicate that power is being supplied to second wall unit 70 and/or the status of a battery included within second wall unit 70.

Second wall unit 70 is adapted to wirelessly receive signals from patient support apparatus 20 and deliver the signals to cable interface 56 in a manner that matches the way the signals would otherwise be delivered to cable interface 56 if a conventional cable were connected between patient support apparatus 20 and cable interface 56. In other words, patient support apparatus 20 and second wall unit 70 cooperate together to provide signals to cable interface 56 in a manner that is transparent to cable interface 56 and room interface board 58 such that they cannot detect whether they are in communication with patient support apparatus 20 via wired or wireless communication. In this manner, a healthcare facility can utilize the wireless communication abilities of one or more patient support apparatuses 20 without having to make any changes to their existing cable interfaces 56 (or to their nurse call system 60 or room interface boards 58).

In at least one embodiment, in addition to sending signals received from patient support apparatus 20 to cable interface 56, second wall unit 70 is also adapted to forward signals received from cable interface 56 to patient support apparatus 20. Second wall unit 70 is therefore adapted, in at least one embodiment, to provide bidirectional communication between patient support apparatus 20 and cable interface 56. Such bidirectional communication includes, but is not limited to, communicating audio signals between a person supported on patient support apparatus 20 and a caregiver positioned remotely from patient support apparatus 20 (which is accomplished by second wall unit 70 forwarding the audio signals of the person on patient support apparatus 20 to nurse call system 60, and vice versa).

Second wall unit 70 communicates the data and signals it receives from patient support apparatus 20 by directing the incoming data and signals it receives to the appropriate pin or pins of cable interface 56. For example, when cable interface 56 includes 37 sockets for coupling to a 37 pin plug, it is common for pins #30 and #31 to be used for indicating a "priority alert," which is often synonymous with an alert that is issued when a patient exits from patient support apparatus 20. Further, depending upon the particular configuration that has been implemented at a particular healthcare facility, the connection between pins #30 and #31 may be normally open or it may be normally closed. Regardless of whether it is normally open or normally closed, whenever second wall unit 70 receives a message from patient support apparatus 20 that a person has exited from patient support apparatus 20, second wall unit 70 will change the status of pins #30 and #31 such that they switch from whatever state they are normally in to their opposite state. Second wall unit 70 therefore reacts to the exit message it receives from patient support apparatus 20 by either opening or closing pins #30 and #31. The nurse call system 60 that is communicatively coupled to cable interface 56 interprets this opening or closing of pins #30 and #31 in the same manner as if a cable were coupled between cable interface 56, such as by sending the appropriate signals to one or more nurse's stations, flashing a light outside the room of patient support apparatus 20, forwarding a call to a mobile communication device carried by the caregiver assigned to the patient of patient support apparatus 20, and/or taking other steps, depending upon the specific configuration of the nurse call system.

In addition to sending data indicating that a patient of patient support apparatus 20 has exited, or is about to exit, therefrom, patient support apparatus 20 is configured, in at least one embodiment, to wirelessly send to second wall unit 70 at least the following additional messages: messages to turn on or off one or more room lights; messages to turn on or off one or more reading lights; messages to increase or decrease the volume of a nearby television set or radio; messages to change a channel of the nearby television set or radio; and messages containing audio packets generated from one or more microphones on the patient support apparatus 20 into which the patient of patient support apparatus 20 speaks when desiring to communicate with a remote caregiver.

In other embodiments, patient support apparatus 20 is configured to wirelessly send to second wall unit 70 any one or more of the following messages, either in addition to or in lieu of any one or more of the messages just mentioned: messages indicating the current status of one or more siderails 34 of patient support apparatus 20 (e.g. whether the side rails are up or down, or have changed position); messages indicating the current status of a brake on patient support apparatus 20; messages indicating the current status of the height of support deck 30 relative to base 22 (e.g. such as whether support deck 30 is at its lowest height or not); messages indicating the current angle of head section 42; messages indicating the current status of an exit detection system (e.g. whether the exit detection system is armed or not); messages indicating the current charging status of one or more batteries on patient support apparatus 20; messages indicating the current status of an alternating current (A/C) power cable on patient support apparatus 20 (e.g. whether it is plugged in or not); diagnostic information about patient support apparatus 20; and/or any other messages containing information about patient support apparatus 20 which may be useful to communicate to a remote location.

In at least one embodiment, second wall unit 70 is further configured to transmit information to cable interface 56 that does not originate from patient support apparatus 20, but instead is generated internally within second wall unit 70. For example, in one embodiment, second wall unit 70 is adapted to forward to cable interface 56 a signal that indicates a "cord-out" alert whenever the communication link between second wall unit 70 and patient support apparatus 20 is unintentionally lost. In many instances, when a conventional cable is coupled between cable interface 56 and a hospital bed, and the cable is inadvertently disconnected, the electrical status of pins 10 and 11 (in a conventional 37 pin connection) will be changed such that the nurse call system will recognize that the cable has become disconnected, and will therefore issue an appropriate alert to the appropriate personnel. Second wall unit 70 is configured to make the same changes to pins 10 and 11 when it unintentionally loses communication with patient support apparatus 20 that would be made to pins 10 and 11 if a cable connection between patient support apparatus 20 and cable interface 56 were to become unintentionally disconnected. Thus, second wall unit 70 and patient support apparatus 20 together include the same ability to provide an indication to cable interface 56 of an unintentional disconnection that exists in some currently-available cable connections to cable interfaces. Still other types of signals that originate from within second wall unit 70 may also be sent to cable interface 56 in addition to, or in lieu of, this cord-out alert.

In addition to forwarding any of the above-described messages or signals to cable interface 56, second wall unit 70 is also adapted, in at least one embodiment, to forward the following messages to patient support apparatus 20 based on information it receives from devices in communication with cable interface 56: messages indicating the establishment and disestablishment of a nurse-call communication link (e.g. messages used for turning on and off a "nurse answer" light on patient support apparatus 20); and messages containing audio packets of a caregiver's voice (generated from a microphone into which the caregiver speaks and forwarded to the appropriate pins of cable interface 56).

In other embodiments, one or more additional messages are also transmitted to patient support apparatus 20 that originate from within second wall unit 70, rather than from any of the devices in communication with cable interface 56. Such messages include any one or more of the following: the charge status of a battery within second wall unit 70 or a battery inside first wall unit 68; acknowledgements of messages transmitted from patient support apparatus 20 to second wall unit 70; and messages used to establish, maintain, and disestablish the communication link between patient support apparatus 20 and second wall unit 70.

As was noted previously, first wall unit 68 and second wall unit 70 may be integrated into a single housing, in some embodiments. FIG. 4 illustrates one such embodiment. Headwall interface 72 includes both first wall unit 68 and second wall unit 70. As shown therein, headwall interface 72 includes a cable interface 88 that is adapted to receive one end of cable 74. The other end of cable 74, as noted, plugs into cable interface 56. In those embodiments of headwall interface 72 where first wall unit 68 and second wall unit 70 are physically separated, cable interface 88 is built into second wall unit 70.

As is also shown in FIG. 4, patient support apparatus 20 includes a first wireless transceiver 90 and a second wireless transceiver 92. First wireless transceiver 90 is adapted to wirelessly communicate with first wall unit 68 and second wireless transceiver 92 is adapted to wirelessly communicate with second wall unit 70. In the embodiment shown in FIG. 4, first transceiver 90 is an infrared transceiver and second transceiver 92 is a Bluetooth transceiver (e.g. IEEE 802.14.1 or standards developed by the Bluetooth Special Interest Group). It will be understood, however, that in other embodiments, first wireless transceiver 90 and/or second wireless transceiver 92 may utilize other forms of Radio Frequency (RF) and non-RF communication. As one example, first transceiver 90 may be implemented as an optical transceiver.

As shown in FIG. 4, patient support apparatus 20 may further include a cable interface 94 that is adapted to couple a cable, which may be of the same type as cable 74, between patient support apparatus 20 and cable interface 56 in those situations where wireless headwall interface 72 is not present, not functional, or otherwise not able to be used. In such situations, patient support apparatus 20 communicates with cable interface 56 directly via the cable coupled to cable interface 94 of patient support apparatus 20 and cable interface 56 of headwall 54.

Figure 5:
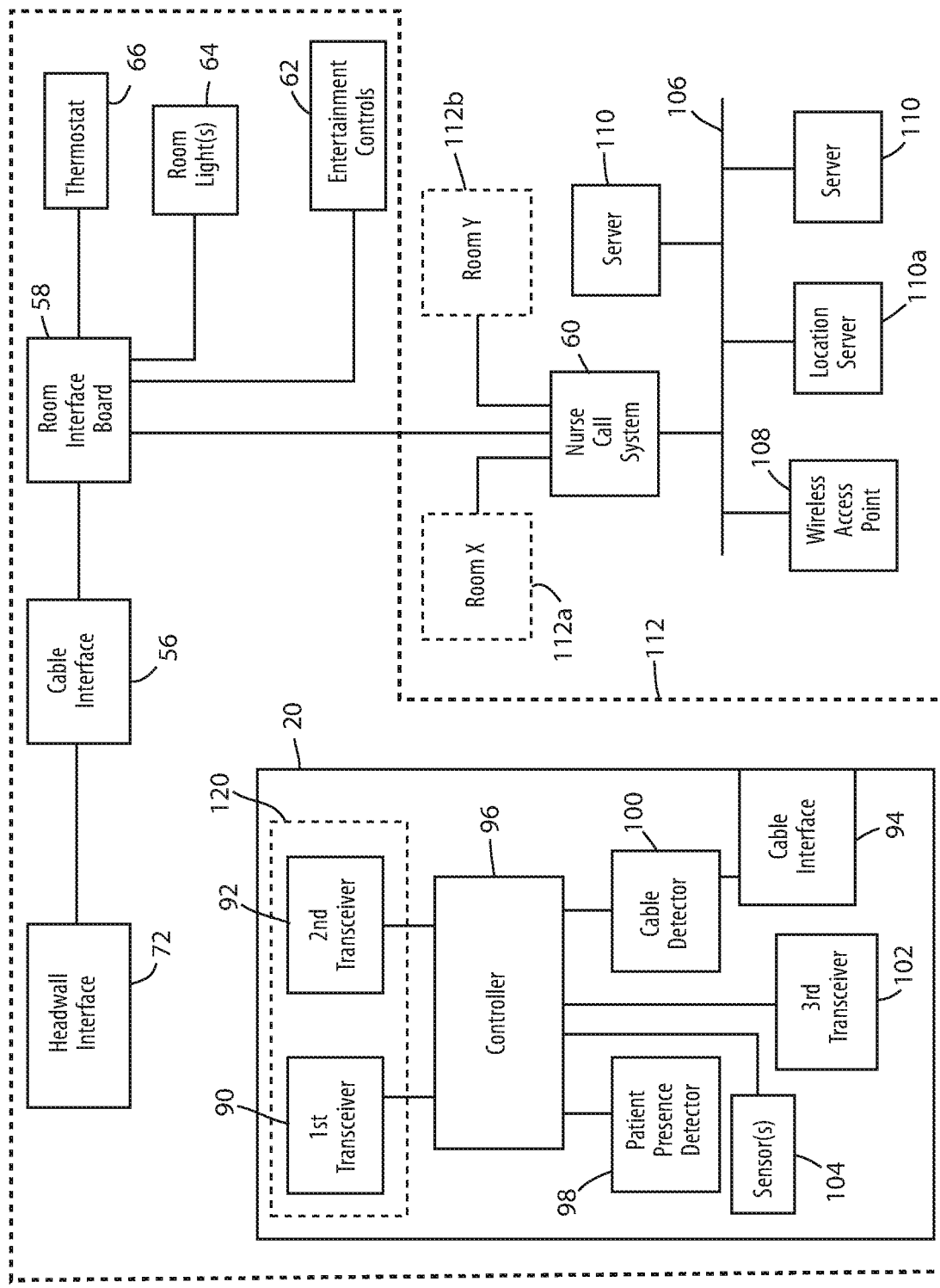
FIG. 5 is a block diagram of the patient support apparatus of FIG. 1 and various components inside and outside of the room in which the patient support apparatus is located.

FIG. 5 illustrates in greater detail various components of patient support apparatus 20, as well as more of the healthcare IT infrastructure 52 that may be present in a particular healthcare facility. With respect to patient support apparatus 20, in addition to cable interface 94 and first and second wireless transceivers 90 and 92, it includes a controller 96, a patient presence detector 98, a cable detector 100, a third transceiver 102, and one or more sensors 104. Controller 96 includes any and all electrical circuitry and components necessary to carry out the functions and algorithms described herein, as would be known to one of ordinary skill in the art. Generally speaking, controller 96 may include one or more microcontrollers, microprocessors, and/or other programmable electronics that are programmed to carry out the functions described herein.

For example, in one embodiment, controller 96 is any one of the i.MX family of system-on-chip (SoC) processors and/or any one of the Kinetis K60 family of microcontroller units (MCUs), both of which are marketed by Freescale Semiconductor of Austin, Tex. Other microcontroller units, however, may be used. Still further, it will be understood that controller 96 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions within patient support apparatus 20, or they may reside in a common location within patient support apparatus 20. When physically distributed, the components may communicate using any suitable serial or parallel communication protocol, such as, but not limited to, CAN, LIN, Firewire, I-squared-C, RS-232, RS-465, universal serial bus (USB), etc. The instructions followed by controller 96 in carrying out the functions described herein, as well as the data necessary for carrying out these functions, are stored in one or more accessible memories (not shown).

Patient presence detector 98 is adapted to automatically detect whether or not a patient is currently present on patient support apparatus 20. The specific components of patient present detector 98 and/or manner in which it detects a patients' presence/absence may vary from embodiment to embodiment. In one embodiment, patient presence detector 98 includes a plurality of force sensors, such as, but not limited to, load cells that detect the weight and/or center of gravity of the patient. Illustrative manners in which such force sensors can be used to detect the presence and absence of a patient, as well as the center of gravity of the patient, are disclosed in the following commonly assigned U.S. patent references: U.S. Pat. No. 5,276,432 issued to Travis and entitled PATIENT EXIT DETECTION MECHANISM FOR HOSPITAL BED; and U.S. patent application Ser. No. 62/253,167 filed Nov. 10, 2015, by inventors Marko Kostic et al. and entitled PERSON SUPPORT APPARATUSES WITH ACCELERATION DETECTION, the complete disclosures of both of which are incorporated herein by reference. Other algorithms for processing the outputs of the force sensors may also be used for detecting a patient's presence and absence.

Patient presence detector 98 may be implemented in other manners in other embodiments. For example, in some embodiments, patient presence detector 98 includes one or more thermal sensors mounted to patient support apparatus 20 that are used to detect the absence/presence of the patient and/or the position of the patient's head on patient support apparatus 20. Further details of such a thermal sensing system are disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

In still other embodiments, patient presence detector 98 detects the absence or presence of a patient using one or more of the methods disclosed in commonly assigned U.S. patent application Ser. No. 14/928,513 filed Oct. 30, 2015, by inventors Richard Derenne et al. and entitled PERSON SUPPORT APPARATUSES WITH PATIENT MOBILITY MONITORING, the complete disclosure of which is also hereby incorporated herein by reference. In yet other embodiments, patient presence detector 98 includes one or more video cameras for detecting the patient's presence, absence, and/or position, such as disclosed in commonly assigned U.S. patent application Ser. No. 14/578,630 filed Dec. 22, 2014, by inventors Richard Derenne et al. and entitled VIDEO MONITORING SYSTEM, the complete disclosure of which is also hereby incorporated herein by reference. In yet another alternative embodiment, the presence, absence, and/or position of a patient is detected using a pressure sensing mat. The pressure sensing mat is positioned on top of the mattress or support deck 30, such as is disclosed in commonly assigned U.S. patent application Ser. No. 14/003,157 filed Mar. 2, 2012, by inventors Joshua Mix et al. and entitled SENSING SYSTEM FOR PATIENT SUPPORTS, the complete disclosure of which is also incorporated herein by reference. In still other embodiments, patient presence detector 98 may take on still other forms.

Cable detector 100 is adapted to detect whether a cable is coupled to cable interface 94 of patient support apparatus 20. Cable detector 100, in at least one embodiment, is implemented as a conventional voltage detector that detects a voltage supplied by the cable when the cable is plugged into cable interface 94. The voltage is supplied by cable interface 56 of headwall 54. Thus, when a cable is coupled between patient support apparatus 20 and cable interface 56 of headwall 54, the cable will have a non-zero voltage on at least one of the pins of the connector that is coupled to cable interface 94 of patient support apparatus 20. Cable detector 100 detects this voltage (or its absence when the cable is not plugged into patient support apparatus 20, or not coupled at its other end to cable interface 56 of headwall 54), and reports the presence/absence of the cable to controller 96. Controller 96 uses this information in any of the manners discussed in greater detail below.

Third transceiver 102 is an optional transceiver that patient support apparatus 20 may include in order to communicate with one or more servers of a healthcare facility network 106 (e.g. a local area network) of the healthcare facility in which patient support apparatus 20 is positioned (FIG. 5). Third transceiver 102 is adapted to communicate with one or more of the servers of healthcare network 106 via one or more of a plurality of access points 108 of healthcare network 106. In some embodiments, third transceiver 102 is a WiFi transceiver (IEEE 802.11) adapted to communicate with access points 108 using any of the various WiFi protocols (IEEE 802.11b, 801.11g, 802.11n, 802.11ac . . . , etc.). In still other embodiments, third transceiver 102 may be adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, third transceiver 102 may take on other forms and/or protocols.

It will be understood that patient support apparatus 20 includes more components than those shown in FIG. 5, and that controller 96 may control more than the components shown in FIG. 5. For example, as noted with respect to FIG. 1, patient support apparatus 20 includes a plurality of user interfaces 50. Those user interfaces may be in direct communication with controller 96 and/or under the control of controller 96, or those user interfaces 50 may be under the control of a separate controller that is, in turn, in communication with controller 96. Patient support apparatus 20 may also include an exit detection system that is under the control of controller 96, or that includes its own controller that communicates with controller 96. One such suitable exit detection system is disclosed in commonly assigned U.S. Pat. No. 5,276,432 issued to Travis and entitled PATIENT EXIT DETECTION MECHANISM FOR HOSPITAL BED, which is incorporated herein by reference, although other types of exit detection systems may be included with patient support apparatus 20. Still other components may be present on patient support apparatus 20 and under the control of controller 96 or another controller onboard patient support apparatus 20.

Patient support apparatus 20 is depicted as being located in a room 112 of a healthcare facility in FIG. 5. The healthcare facility may include additional rooms 112a, 112b, etc. that are similar to room 112. That is, each room may include one or more headwall interfaces 72, and each headwall interface 72 is in communication with a cable interface 56 and the room interface board 58 for that particular room. The room interface boards 58, in turn, are in communication with the thermostat 66, room lights 64, and entertainment controls 62 for that particular room. Still further, each room interface board 58 is coupled to the nurse call system 60. The nurse call system 60, in some embodiments, is in communication with the healthcare facility computer network 106.

Healthcare facility computer network 106 includes a plurality of servers 110. Although not shown, healthcare facility computer network 106 may include an Internet server and/or an Internet gateway that couples network 106 to the Internet, thereby enabling servers 110, patient support apparatuses 20, and other applications on network 106 to communicate with computers outside of the healthcare facility, such as, but not limited to, a geographically remote server operated under the control of the manufacturer of patient support apparatuses 20. Computer network 106 also includes a location server 110a that is adapted to monitor and record the current locations of patient support apparatuses 20 within the healthcare facility. Location server 110a is in communication with the patient support apparatuses 20 via access points 108 and third transceiver 102. In some embodiments, location server 110a shares the location of the patient support apparatuses 20a with other applications and/or servers on network 106. Still further, in some embodiments, location server 110a records a location history of each of the patient support apparatuses 20 for later retrieval by authorized personnel and/or authorized servers 110. Further description of location server 110a is provided below.

It will be understood by those skilled in the art that the particular components of network 106 shown in FIG. 5 may vary widely. For example, although FIG. 5 shows nurse call system 60 coupled to network 106, this may be varied. Further, network 106 may include a conventional Admission, Discharge, and Tracking (ADT) server that allows patient support apparatuses 20 to retrieve information identifying the patient assigned to a particular patient support apparatus 20. Location server 110a may also forward location information regarding the current location each of patient support apparatuses 20 to the ADT server. Healthcare network 106 may also be in communication with a conventional Electronic Medical Records (EMR) server such that patient support apparatuses 20 are able to send data to, and retrieve data from, the EMR server via third transceiver 102. Still further, healthcare network 106 may further include one or more conventional work flow servers and/or charting servers that assign, monitor, and/or schedule patient-related tasks to particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20.

Sensors 104 of patient support apparatus 20 may take on a variety of different forms. In some embodiments, as will be discussed in greater detail below, sensors 104 include any one or more of the following: a brake sensor adapted to detect whether or not a caregiver has applied a brake to patient support apparatus 20; a height sensor adapted to detect the height of support deck 30 (and/or detect whether support deck 30 is at its lowest height or not); siderail sensors adapted to detect whether siderails 34 are in their raised or lowered orientations; an exit detection status sensors adapted to detect whether an exit detection system on board patient support apparatus 20 is armed or not; a microphone adapted to detect the voice of patient positioned on patient support apparatus 20 so that the patient can communicate aurally with a remotely positioned caregiver (via nurse call system 60); and/or another type of sensor.

First and second transceivers 90 and 92 of patient support apparatus 20 are adapted to communicate wirelessly with the headwall interface 72 that is positioned in the same room that patient support apparatus 20 is currently located in. As noted previously, headwall interface 72 includes first wall unit 68 and second wall unit 70, and these wall units may be combined together into a single unit having a single, common housing, or they may be separate units (such as shown in FIG. 2). Regardless of whether they are separated or integrated together, first and second wall units 68 and 70 of headwall interface 72 are adapted to communicate with first and second transceivers 90 and 92, respectively, of patient support apparatus 20.

Figure 6:
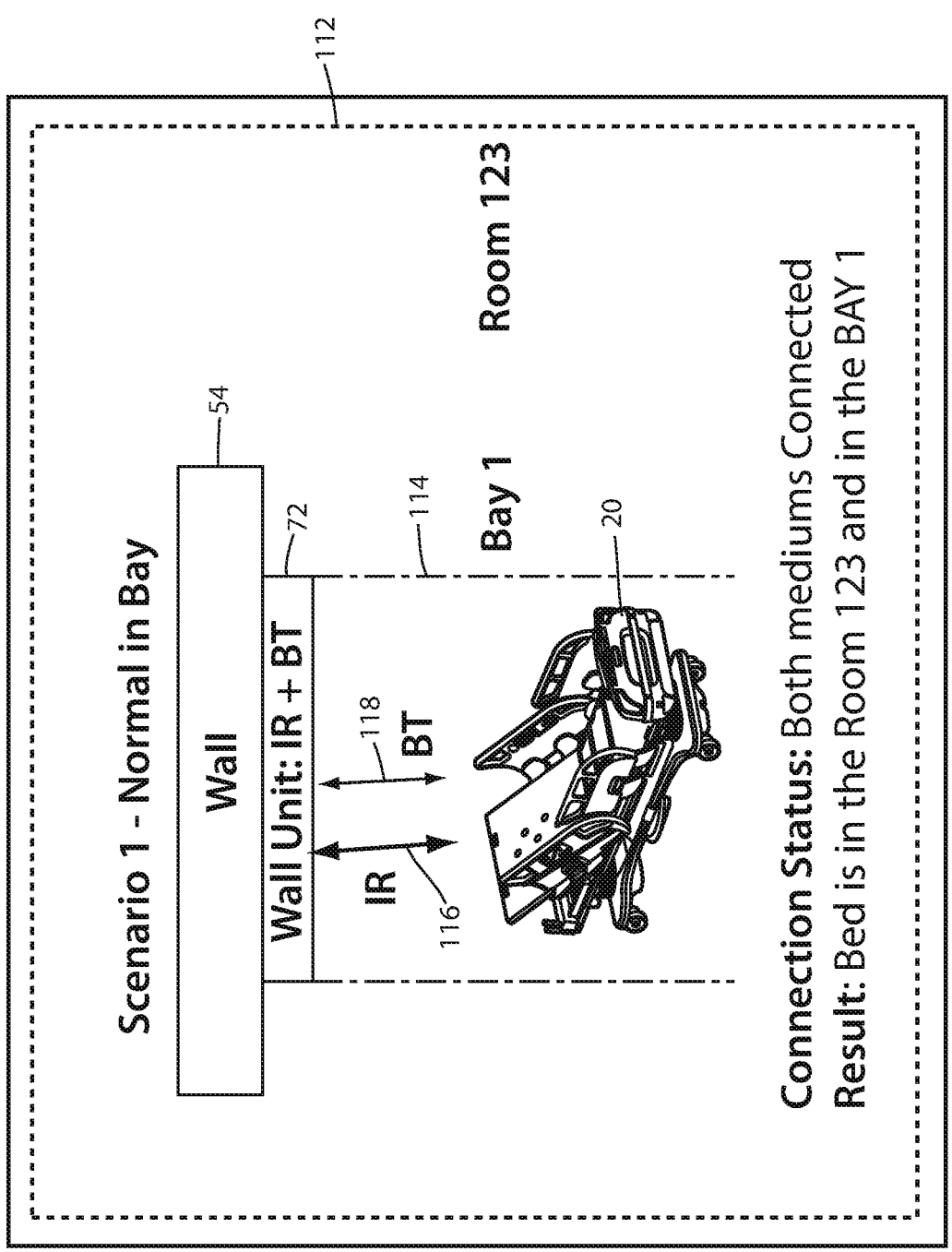
FIG. 6 is a block diagram of the patient support apparatus of FIG. 1 shown communicating in a normal state with a headwall interface.

As is illustrated in more detail in FIGS. 6-9 and discussed more below, first and second transceivers 90 and 92 are utilized by controller 96 of patient support apparatus 20 to communicate information wirelessly from patient support apparatus 20 to room interface board 58 and to determine the location of, and communication status of, patient support apparatus 20 with respect to cable interface 56. As is shown in FIG. 6, a typical healthcare facility room 112 includes a headwall 54 having a headwall interface 72 and at least one bay area 114. Bay area 114 refers to the area in front of, or adjacent to, headwall interface 72 and is the area where the patient support apparatus 20 typically remains when it is positioned within that particular room 112. In some healthcare facilities, one or more of the rooms are single patient support apparatus rooms in which only a single patient support apparatus is present (private rooms). In such rooms, there is only one bay. Healthcare facilities, however, typically include one or more rooms in which multiple patient support apparatuses 20 are positioned (semi-private rooms). In such rooms, there are multiple bays 114 for the multiple patient support apparatuses 20.

First and second transceivers 90 and 92 act to wirelessly replace the conventional nurse-call cable that runs from patient support apparatus 20 to cable interface 56. That is, first and second transceivers 90 and 92 allow patient support apparatus 20 to wirelessly communicate with room interface board 58 (and all of the components in communication with room interface board 58) without having to run a cable between patient support apparatus 20 and cable interface 56. This eliminates a caregiver task that would otherwise need to be completed, thereby improving the efficiency of the healthcare staff.

When patient support apparatus 20 is positioned within a bay 114 and in normal communication with headwall interface 72, both of the transceivers 90 and 92 are in communication with both of the wall units 68 and 70. That is, first transceiver 90 is in communication with first wall unit 68 and second transceiver 92 is in communication with second wall unit 70. As was noted previously, first wall unit 68 and first transceiver 90 are both adapted, in at least one embodiment, to communicate using infrared signals. Although other types of communication may be used, the following additional description of these two components (first transceiver 90 and first wall unit 68) will be carried out under the assumption that these two components communicate using infrared. It will be understood, however, that this is not intended to limit the communication medium for these two components and that other types of communication besides infrared are possible. Similarly, although other types of communication may be used between second transceiver 92 and second wall unit 70, for purposes of the following written description it will be assumed that these two components communicate using conventional Bluetooth technology. This written description is not to be interpreted as an indication that other types of communication cannot be used between second transceiver 92 and second wall unit 70.

When a patient support apparatus 20 is properly positioned within a bay 114 relative to headwall interface 72, both of the transceivers 90 and 92 are able to communicate with headwall interface 72. If patient support apparatus 20 is positioned outside of the bay area 114, first transceiver 90 will not be able to communicate with first wall unit 68 of headwall interface 72 because first transceiver 90 uses infrared signals, which are line-of-sight signals, and first wall unit 68 is set up such that its line-of-sight signals are only detectable when the patient support apparatus is positioned within the corresponding bay 114, or a portion of that bay 114. Accordingly, when controller 96 determines that first transceiver 90 is able to successfully communicate with a first wall unit 68 of a headwall interface 72, it concludes that the patient support apparatus 20 is positioned adjacent to the headwall interface 72.

Second transceiver 92 is able to communicate with second wall unit 70 when patient support apparatus 20 is positioned outside of bay area 114 because second transceiver 92 is a Bluetooth transceiver that uses radio frequency (RF) waves that are not line-of-sight. Accordingly, patient support apparatus 20 does not need to be in bay area 114 to communicate with second wall unit 70. However, the power levels of the Bluetooth communication used by second wall unit 70 are set such that patient support apparatus 20 is not generally able to communicate with a headwall interface 72 when the patient support apparatus is positioned outside of the room in which the headwall interface 72 is positioned. As a result, when controller 96 establishes communication with headwall interface 72 using second transceiver 92, controller 96 knows that it is currently positioned within the same room as the headwall interface (or very close by). Further, when controller 96 establishes communication with headwall interface 72 using first transceiver 90, controller 96 knows that patient support apparatus 20 is currently positioned within the bay area 114 associated with that particular headwall interface 72. Accordingly, controller 96 is able to confirm its position within a particular room using two sources of information.

Each headwall interface 72 includes a unique identifier that uniquely identifies that particular headwall interface 72 from the other headwall interfaces 72 within the healthcare facility. When first transceiver 90 is able to communicate with first wall unit 68, the unique identifier from the headwall interface 72 is transmitted from headwall interface 72 to the patient support apparatus 20. Similarly, when second transceiver 92 is able to communicate with second wall unit 70, the same unique identifier from the headwall interface 72 is transmitted to patient support apparatus 20. Controller 96 of patient support apparatus 20 either sends the unique identifier to location server 110*a* via third transceiver 102 (and location server 110*a* then converts the identifier into a location via a look-up table it has access to that correlates all of the headwall interface 72 identifiers within the healthcare facility to their respective locations), or controller 96 consults an on-board look-up table that correlates the unique identifiers to locations within the healthcare facility. In the former case, controller 96 sends the identifier and in the latter case, controller 96 sends its actual location. The identifier or location is sent to location server 110*a* and/or to other servers/applications on computer network 106.

FIG. 6 depicts the communication of patient support apparatus 20 with both first wall unit 68 and second wall unit 70. This is shown by an infrared communication link 116 between first wall unit 68 and first transceiver 90, as well as a Bluetooth communication link 118 between second wall unit 70 and second transceiver 92. When both of these communication links 116 and 118 are established, controller 96 sends a message to location server 110*a* and/or another server on network 106 indicating that it has established normal communications with headwall interface 72. An additional message may also be sent, as mentioned earlier, that specifies the unique identifier of that particular headwall interface 72.

Figure 7:
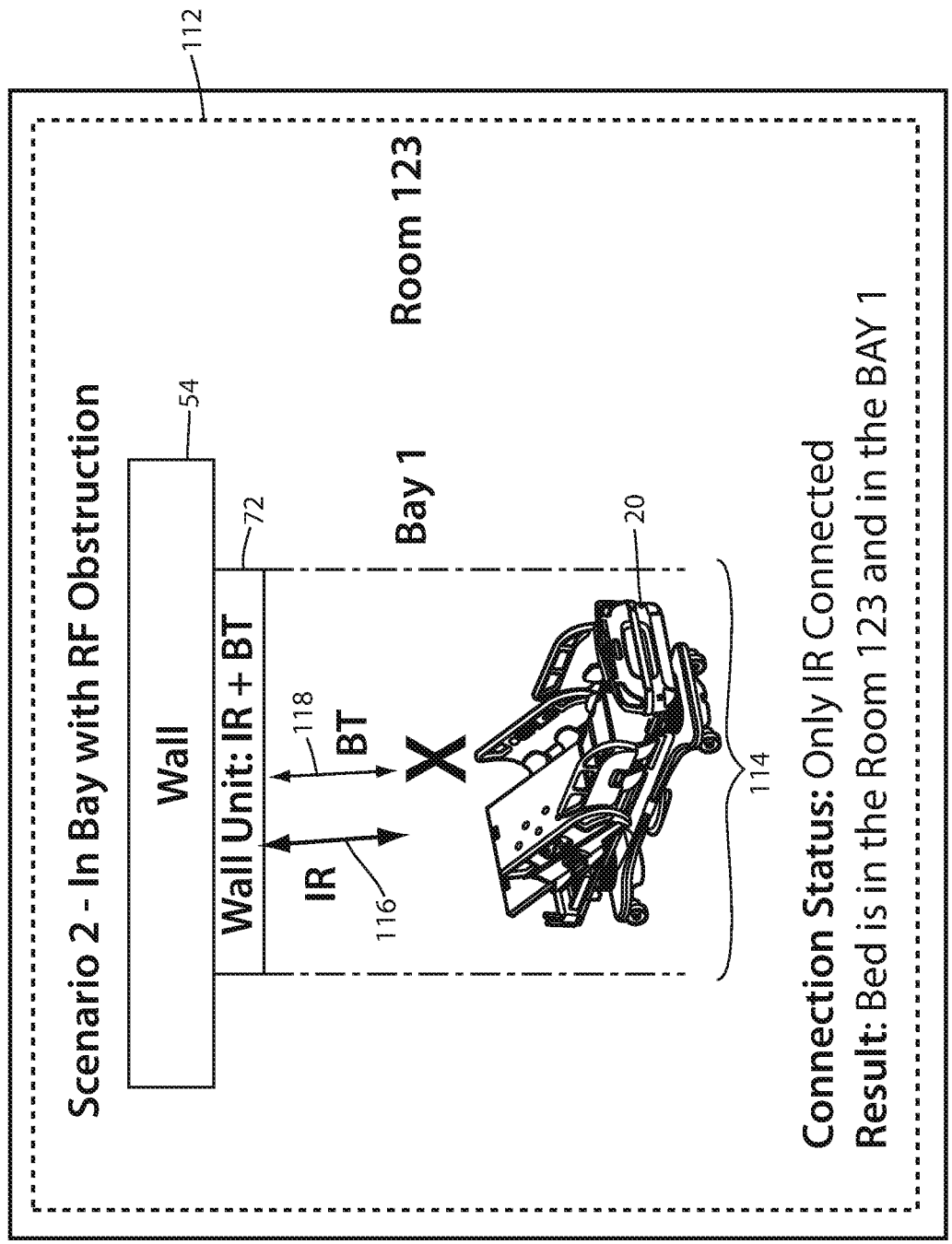
FIG. 7 is a block diagram of the patient support apparatus of FIG. 1 shown with an RF obstruction in its communication with the headwall interface.

FIG. 7 illustrates a situation where patient support apparatus 20 is unable to establish communication using both communication links 116 and 118. In this particular situation, controller 96 is only able to establish IR communication link 116. Bluetooth communication link 118 is not established due to an obstruction within the room 112. In this situation, controller 96 is able to determine its location (both a specific room 112 and a specific bay area 114) within the healthcare facility because it is able to establish communication link 116, which, as noted, is a line-of-sight communication link that is designed to only operate when patient support apparatus 20 is in that particular bay 114.

In the situation of FIG. 7, controller 96 is programmed to send a message to location server 110*a* and/or another server of network 106 via third transceiver 102 indicating its room and bay location within healthcare facility, as well as a message indicating that an error is present with respect to Bluetooth communication link 118. The recipient of this message, in some embodiments, is programmed to forward this message to nurse call system 60, as asset tracking system coupled to network 106, and/or a mobile communication system that is able to relay this message to a particular healthcare worker carrying a mobile communication device (e.g. cell phone, pager, laptop, tablet computer, etc.). An appropriate healthcare worker is thereby notified that a communication error is present between patient support apparatus 20 and headwall interface 72. The communication error does not prevent patient support apparatus 20 from successfully communicating with headwall interface 72 (via first communication link 116) and room interface board 58, but it may reduce the functionality of the communication (for example audio communication between patient support apparatus 20 and headwall interface 72 may have reduced quality because of reduced bandwidth in communication link 116.

Figure 8:
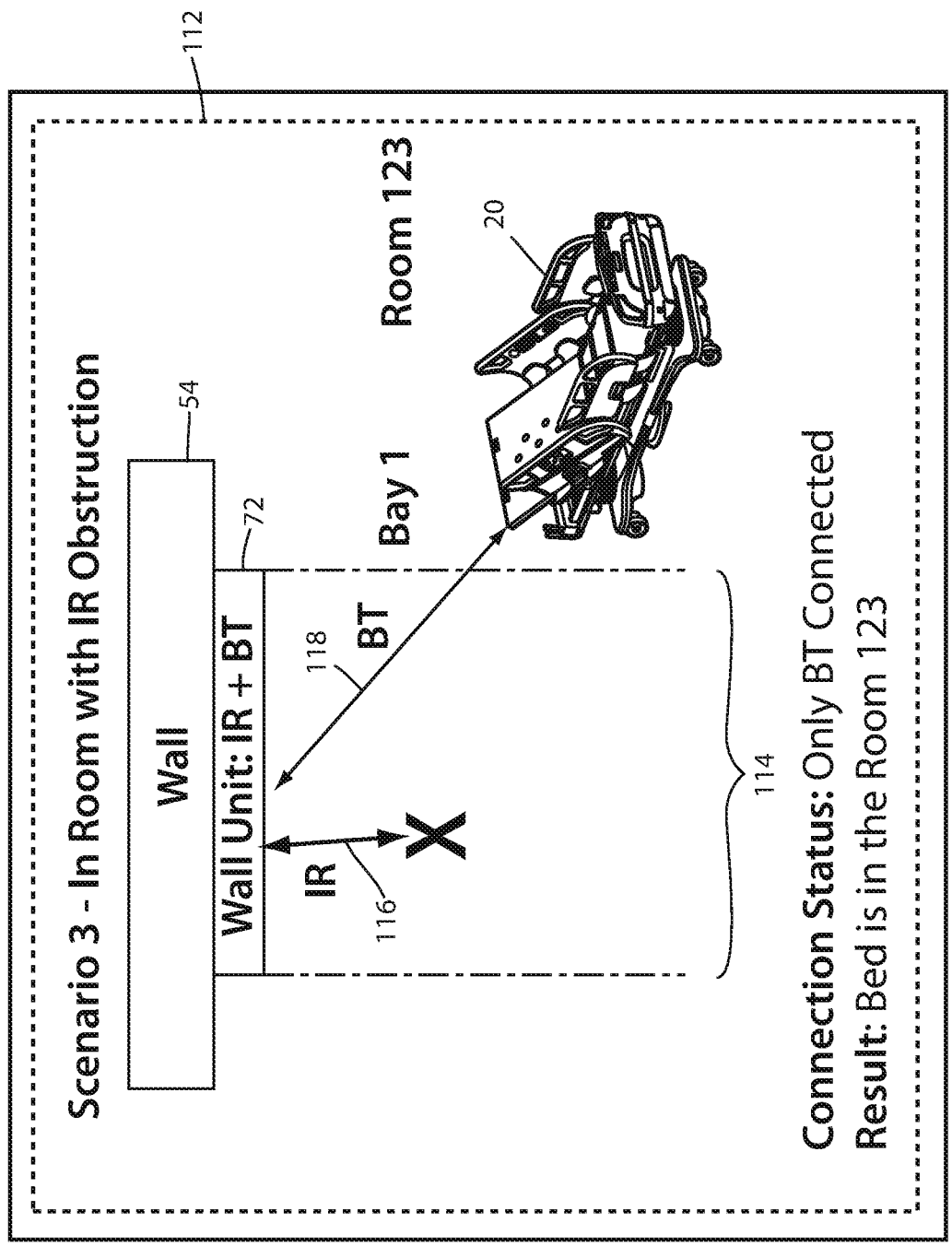
FIG. 8 is a block diagram of the patient support apparatus of FIG. 1 shown positioned out of range of an infrared communication transceiver of the headwall interface.

FIG. 8 illustrates another situation where patient support apparatus 20 is unable to establish communication using both communication links 116 and 118. In this particular situation, controller 96 is only able to establish Bluetooth communication link 118. Infrared communication link 116 is not established due to patient support apparatus 20 being located outside of bay area 114 of room 112. In other words, patient support apparatus 20 is positioned at a location where there is no line-of-sight path between IR transceiver 90 and first wall unit 68.

In the situation of FIG. 8, controller 96 is programmed to send a message to location server 110*a* and/or another server of network 106 indicating its room location within healthcare facility, but not its bay location. In some embodiments, if IR communication link 116 is not established within a predetermined amount of time after establishing Bluetooth communication link 118, controller 96 is programmed to send a message to location server 110*a* (and/or another server 110 on network 106) indicating that a likely malfunction has occurred with respect to communication link 116. The predetermined amount of time is chosen to account for the typical amount of time it takes between patient support apparatus 20 establishing communication link 118 and establishing communication link 116 when the patient support apparatus 20 is initially moved into a room. In other words, if patient support apparatus 20 is positioned within room 112 for more than a predetermined time, controller 96 assumes that any failure to establish communication link 116 is not due to patient support apparatus 20 simply being out of range of first wall unit 68, but instead is due to a malfunction in communication link 116.

When controller 96 determines its room location via communication link 118 but does not establish communication link 116, it is programmed in some embodiments to forward a message to location server 110*a* (and/or another server on network 106) via third transceiver 102 indicating its room location (or simply the unique identifier of headwall interface 72) and an error in its ability to establish communications via communication link 116. In some embodiments, the sending of this error message is delayed for a predetermined time period in order to allow controller 96 to determine whether the error is due to a communication malfunction or is due to the patient support apparatus 20 being moved into or out of the room 112, as will be discussed in more detail below. The recipient of this message, in some embodiments, is programmed to forward this message to nurse call system 60, an asset tracking system, and/or a mobile communication system that is able to relay this message to a particular healthcare worker carrying a mobile communication device (e.g. cell phone, pager, laptop, tablet computer, etc.). An appropriate healthcare worker is thereby notified that a communication error is present between patient support apparatus 20 and headwall interface 72. The communication error does not prevent patient support apparatus 20 from successfully communicating with headwall interface 72 (via second communication link 118) and room interface board 58, but it may reduce the functionality of the communication or it may impact other aspects of the operation of the healthcare facility (for example patient support apparatus 20 may not be able to automatically distinguish which bay of the room it is located in, and an association between that bay and a particular patient may not be able to be automatically established.)

Figure 9:
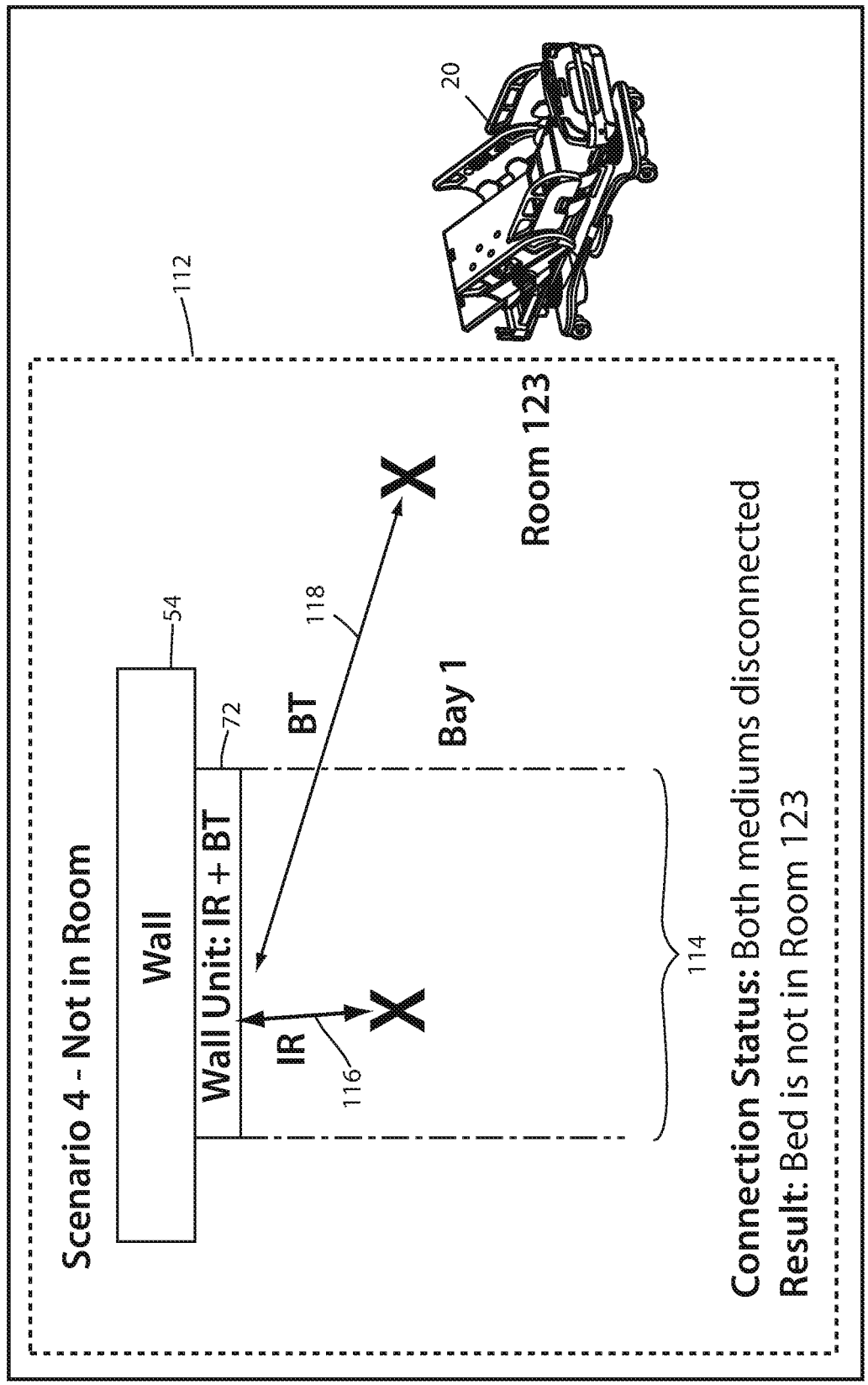
FIG. 9 is a block diagram of the patient support apparatus of FIG. 1 shown positioned out of range of both transceivers of the headwall interface.

FIG. 9 illustrates a situation where patient support apparatus 20 is positioned outside of room 112 and therefore is unable to establish either first communication link 116 or second communication link 118. In this particular situation, controller 96 is programmed to send a message to location server 110*a* and/or an asset tracking system or other server on network 106 indicating it is not currently located in a room with a headwall interface 72. The message is sent via third transceiver 102. In some embodiments, when patient support apparatus 20 is not positioned in a room, such as the situation illustrated in FIG. 9, patient support apparatus 20 is configured to determine its location with the healthcare facility using other means. For example, in some embodiments, patient support apparatus 20 is configured to determine its non-room location using triangulation and/or trilateration with respect to the known position of the multiple access points 108. Examples of patient support apparatuses configured to perform this type of location detection are disclosed in commonly assigned U.S. patent application Ser. No. 14/559,458 filed Dec. 3, 2014, by inventors Michael Hayes et al. and entitled PATIENT SUPPORT APPARATUS COMMUNICATION SYSTEMS, the complete disclosure of which is incorporated herein by reference. Other types of supplemental location-detection systems may also be included with patient support apparatus 20 in order to detect its location when it is not positioned within a room, or otherwise in communication range of a headwall interface 72.

First and second transceivers 90 and 92 of patient support apparatus are, in some embodiments, used as a movement detector 120 (FIG. 5) that is adapted to detect whether patient support apparatus 20 is in the process of leaving a room or entering a room. In such embodiments, not only is patient support apparatus 20 configured to determine its room location and bay location, but it is also configured to detect whether it is in the process of being moved out of a room or being moved into a room. The manner in which first and second transceivers 90 and 92 are used in order to detect this ingress into and egress out of a room is described in more detail below with respect to FIGS. 10 and 11.

Figure 10:
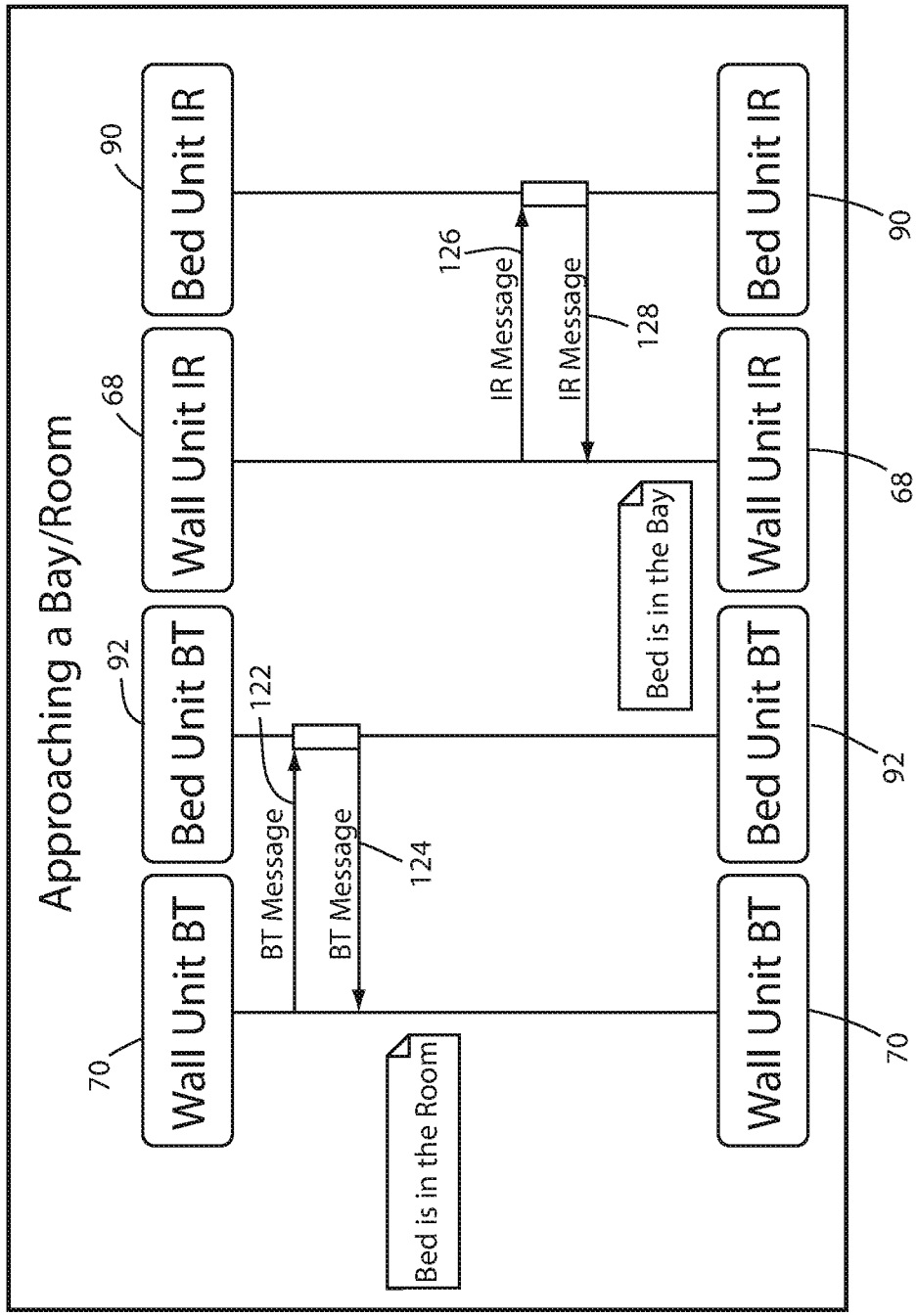
FIG. 10 is a communication diagram showing an example of headwall communication when the patient support apparatus is entering a room or bay of a room.

FIG. 10 illustrates in more detail one manner in which controller 96 utilizes first and second transceivers 90 and 92 to detect when patient support apparatus 20 is in the process of being, or recent has been, moved into a room 112 and/or into a bay area 114 of a room 112. When patient support apparatus 20 first enters room 112, second wall unit 70 sends out an inquiry message at step 122. The inquiry message is received by second transceiver 92 of patient support apparatus 20. Such inquiry messages are sent periodically and repetitively by second wall unit 70, in at least some embodiments. Upon receiving this inquiry message, second transceiver 92 responds at step 124 with an acknowledgement message. At this point in time, controller 96 may determine that patient support apparatus 20 is entering a room 112 because it was not in communication with a second wall unit 70 or a first wall unit 68 immediately prior to the sending of the inquiry message at step 122. In other words, the initial commencement of communication with a second wall unit 70—along with the fact that no communication link 116 has yet been established between first wall unit 68 and first transceiver 90—may be interpreted by controller 96 as an indication that patient support apparatus 20 is entering a room. As will be discussed in more detail below, this determination of room entry may be supplemented with additional information received by controller 96 in order to provide a more robust conclusion that patient support apparatus 20 has entered a room.

At some point after patient support apparatus 20 enters a room 112, the person controlling the movement of patient support apparatus 20 will move patient support apparatus 20 into a bay area 114. First wall unit 68 is configured, in at least some embodiments, to also send out periodic inquiry messages, such as shown in FIG. 10 at step 126. When patient support apparatus 20 is in a bay area 114, it receives the inquiry message sent at step 126 and responds to the inquiry message with an acknowledgement message at step 128. After this exchange of messages at steps 126 and 128, controller 96 concludes that patient support apparatus 20 is now positioned within the bay area 114 associated with the particular headwall interface 72 that it is currently in communication with (the inquiry message sent at step 126 includes the unique identifier associated with the headwall interface 72 of which first wall unit 68 is a part).

Thus, by monitoring the sequence in which first and second transceivers 90 and 92 establish communication with a headwall interface 72, controller 96 is able to determine when patient support apparatus 20 is moving into a room. When controller 96 sees that communication is established between second wall unit 70 and second transceiver 92, followed by subsequent communication being established between first wall unit 68 and first transceiver 90, controller 96 concludes that patient support apparatus 20 has just entered a room. As will be explained in greater detail below, controller 96 is configured in some embodiments to take one or more steps automatically in response to the determination that patient support apparatus 20 has just entered a room.

As was noted previously, controller 96 may utilize supplemental information beyond that discussed above to determine when patient support apparatus 20 has entered a room 112. This supplemental information may come from a variety of different sources, including, but not limited to, one or more of sensors 104. For example, in some embodiments, controller 96 is configured to check the status of the brake of patient support apparatus. If the brake is currently being applied, then controller 96 does not conclude that patient support apparatus 20 has just entered a room because such movement is highly unlikely when the brake is applied. Similarly, patient support apparatus 20 may be equipped with one or more sensors 104 that detect motion of patient support apparatus 20, such as one or more wheel encoders, accelerometers, magnetometers, inertial sensors, signal strength monitors that monitor the signal strength of communications with access points 108, etc. If such motion sensors do not indicate any motion is taking place, then controller 96 does not conclude patient support apparatus 20 has just entered a room, even if communication is established with first and second wall units 68 and 70 in the order depicted in FIG. 10. However, if such motion sensors do indicate motion is detected, and communication is established in the order shown in FIG. 10, this provides confirmation to controller 96 that patient support apparatus 20 has indeed entered a room 112.

Figure 11:
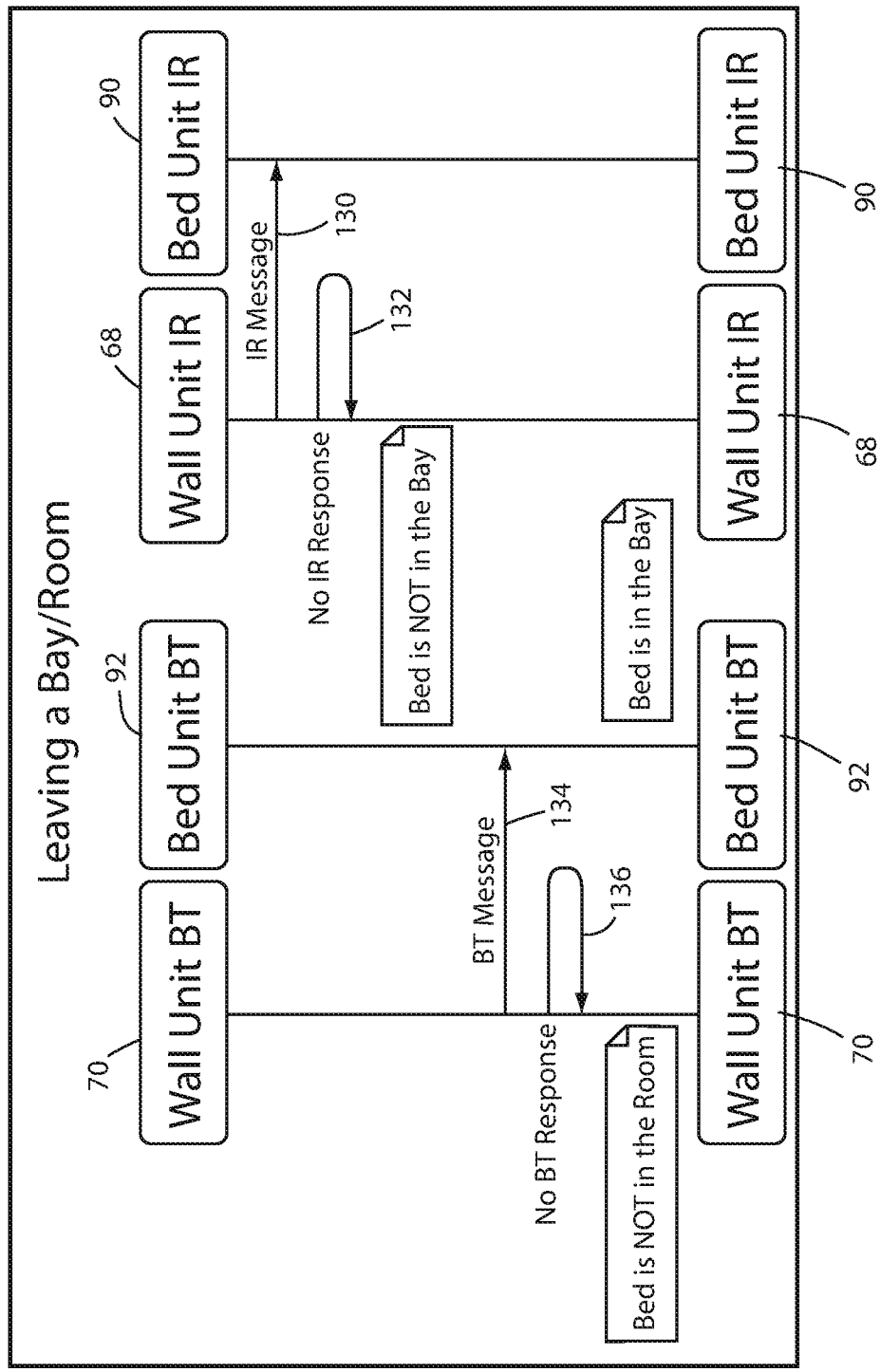
FIG. 11 is a communication diagram showing an example of headwall communication when the patient support apparatus is leaving a room or bay of a room.

FIG. 11 illustrates in more detail one manner in which controller 96 utilizes first and second transceivers 90 and 92 to detect when patient support apparatus 20 is in the process of being moved out of, or has recently exited, a room 112 and/or a bay area 114. When communication links 116 and 118 are established between patient support apparatus 20 and headwall interface 72, periodic messages, such as heartbeat messages, are repetitively exchanged between patient support apparatus 20 and headwall interface 72. In some embodiments, controller 96 is adapted to send a message to location server 110a or another server 110 on network 106 indicating the successful establishment of communication links 116, 118, as confirmed by the successful transmission of one or more heartbeat messages. Controller 96 is also configured to monitor the sequence in which these heartbeat messages are terminated and to use that sequence to determine when a patient support apparatus is in the process of leaving, or has already left, a room.

As shown in FIG. 11, first wall unit 68 sends one of its periodic messages to first transceiver 90 of patient support apparatus 20 at step 130. Patient support apparatus 20 does not receive this message because it has moved outside of the bay area 114 in which such messages are receivable. Accordingly, at step 132, controller 96 determines that a periodic message from first wall unit 68 has not been received and that patient support apparatus is no longer in bay area 114. At a subsequent step 134, second wall unit 70 sends out a periodic message (as it is configured to repetitively do) to patient support apparatus 20. As illustrated by step 136, this message is not received by patient support apparatus 20. The failure to receive this message is used by controller 96 to conclude that patient support apparatus 20 has moved out of range of second wall unit 70, and this range, as noted, generally corresponds to room 112.

Controller 96 is therefore configured to conclude that patient support apparatus 20 is moving out of a room based on the order in which communication links 116 and 118 are disestablished. As shown in FIG. 11, when first communication link 116 is first disestablished followed by second communication link 118 being disestablished, controller 96 concludes that patient support apparatus 20 is moving out of, or has already moved out of, a room 112. As with the determination that patient support apparatus 20 is moving into a room (described above), controller 96 may utilize any of the supplemental motion detection sensors mentioned above to confirm that such movement is or has occurred, or to conclude that such movement is or has not occurred. Still further, as with the determination that patient support apparatus 20 has entered a room, controller 96 is configured to automatically take one or more actions in response to determining that patient support apparatus 20 has exited a room, as will be discussed in more detail below.

It will be understood by those skilled in the art that the specific sequence of messages shown in FIGS. 10 and 11 may be modified from that shown when concluding that a patient support apparatus 20 is entering or exiting a room. For example, although FIG. 10 illustrates an initial message being sent at step 122 from second wall unit 70 to second transceiver 92, it will be understood that this may be reversed. That is, instead of second wall unit 70 sending out periodic messages that are detected by second transceiver 92, second transceiver 92 may be configured to send out periodic messages that are detected by second wall unit 70. The same is true for the messages sent at steps 126 and 128 in FIG. 10. That is, first transceiver 90 may send out an inquiry message at step 126 and first wall unit 68 may respond to it at step 128. This reversal of messages may also be applied to what is shown in FIG. 11. That is, instead of first wall unit 68 sending out a message at step 130 that is not received and/or instead of second wall unit 70 sending out a message at step 134 that is not received, either of these messages may alternatively be sent by first transceiver 90 and second transceiver 92, respectively. Thus, the particular order in which messages are transmitted between first transceiver 90 and first wall unit 68 are not important, nor is the order in which the messages are transmitted between second transceiver 92 and second wall unit 70 important. Instead, it is the order in which communication links 116 and 118 are established or disestablished with respect to each other that is used by controller 96 to determine whether patient support apparatus 20 is entering or exiting a room.

As yet another modification to the messages illustrated in FIGS. 10 and 11, it will be understood that more than the single messages illustrated therein may be sent by each of components 68, 70, 90, and 92. That is, for example, it may take multiple messages (e.g. several of steps 122 and 124) in FIG. 10 between second wall unit 70 and second transceiver 92 before controller 96 concludes that patient support apparatus 20 is in a room and/or before communication link 118 is established. Similarly, steps 126 and 128 may be repeated one or more times before controller 96 determines that patient support apparatus 20 is in a particular bay area 114. With respect to FIG. 11, controller 96 may be programmed to conclude that a communication link 116 and/or 118 is not disestablished until multiple periodic messages are not received, rather than concluding a communication link has been disestablished based upon the lack of receipt of only a single periodic message. Still other modifications may be made to the messages illustrated in FIGS. 10 and 11 and described above when controller 96 determines whether patient support apparatus 20 is moving into or out of a room.

In some embodiments, controller 96 is configured to automatically take one or more steps in response to its determination that patient support apparatus 20 has just entered a room. These automatic steps include any one or more of the following: sending a command to room lights 64 (via headwall interface 72, cable interface 56, and room interface board 58) to turn on; sending a command to entertainment controls 62 (via headwall interface 72, cable interface 56, and room interface board 58) to turn on a television or a radio, or to turn up a volume of the television or radio; sending a command to thermostat 66 (via headwall interface 72, cable interface 56, and room interface board 58) to change a temperature setting, or to start or stop heating or cooling; sending a notification message to location server 110a (via third transceiver 102 and wireless access points 108) indicating that patient support apparatus 20 has entered a room; terminating a power saving mode; turning on one of more displays or other indicators on the patient support apparatus 20; turning on a nightlight on patient support apparatus 20; turning on power to a mattress 40 positioned on patient support apparatus 20; turning on power to one or more amplifiers on patient support apparatus 20 (e.g. amplifiers for a radio or for nurse-call communication) and/or other actions.

Still further, controller 96 may be configured to automatically remind a caregiver to couple patient support apparatus 20 to a power supply (e.g. an electrical wall outlet) when controller 96 determines that is has just entered a room. This reminder may take the form of a message displayed on a display of patient support apparatus 20, or it may take on other forms, such as the illumination of one or more lights, the emission of one or more sounds, and/or other forms. In some embodiments, controller 96 is configured to send a message to a server 110 of computer network 106 if an electrical cable is not coupled between patient support apparatus 20 and an electrical wall outlet a predetermined amount of time after patient support apparatus 20 has been moved into a room. The recipient server 110 is programmed to forward the message to one or more caregivers associated with that particular patient support apparatus 20 (or a patient assigned to that patient support apparatus 20) reminding the caregiver to plug in the patient support apparatus 20 to a power supply. The message may be forwarded using a conventional communication server 110 on network 106.

In some healthcare settings, administrative personnel may decide that patient support apparatuses 20 are preferred to communicate with nurse call system 60 via a cable rather than wirelessly. In other words, administrative personnel may prefer to have a cable coupled between patient support apparatus 20 and cable interface 56, rather than utilize the wireless communication between patient support apparatus 20 and headwall interface 72. In such embodiments, controller 96 is configurable to issue a reminder to caregivers to couple a nurse call cable between patient support apparatus 20 and cable interface 56 when it is determined that patient support apparatus 20 has just entered a room. As with the reminder to plug in a power cable mentioned above, the nurse call cable reminder may take on a variety of different forms, including a message on a display, one or more audio or visual indications, and/or a message to a server 110 on network 106 capable of forwarding message to mobile electronic devices carried by caregivers. When controller 96 is configured to issue a nurse call cable reminder, controller 96 may be configured by appropriate personnel to issue the nurse call cable reminder in one or more particular rooms, and/or more particular sets of rooms, floors, wings, and/or for the entire healthcare facility. In other words, the nurse call cable reminder may be issued by controller 96 only in some rooms, or it may be issued in all of the rooms of the healthcare facility In some embodiments, any one or more of the actions automatically undertaken by controller 96 in response to detecting patient support apparatus 20 has entered a room are modified to be contingent upon whether or not a patient is present on patient support apparatus 20, as detected by patient presence detector 98. For example, if no patient is present when a patient support apparatus 20 is moved into a room, then controller 96 is configured in some embodiments to skip automatically performing one or more of the following actions: sending a command to turn on a television or radio (or turn up the volume of the television or radio); sending a command to thermostat 66; sending a command to room lights 64; terminating a power saving mode; turning on one of more displays or other indicators on the patient support apparatus 20; turning on a nightlight on patient support apparatus 20; turning on power to a mattress 40 positioned on patient support apparatus 20; turning on power to one or more amplifiers on patient support apparatus 20 (e.g. amplifiers for a radio or for nurse-call communication) and/or other actions. Other changes may be implemented based on the presence or absence of a patient on patient support apparatus 20.

Controller 96 is also configured in some embodiments to automatically take one or more steps in response to its determination that patient support apparatus 20 is exiting, or has just exited, a room 112. These automatic steps include any one or more of the following: sending a command to room lights 64 (via headwall interface 72, cable interface 56, and room interface board 58) to turn off; sending a command to entertainment controls 62 (via headwall interface 72, cable interface 56, and room interface board 58) to turn off a television or a radio, or to turn down a volume of the television or radio; sending a command to thermostat 66 (via headwall interface 72, cable interface 56, and room interface board 58) to change a temperature setting, or to start or stop heating or cooling; sending a notification message to location server 110a (via third transceiver 102 and wireless access points 108) indicating that patient support apparatus 20 has exiting a room; entering a power saving mode; shutting off one of more displays or other indicators on the patient support apparatus 20; turning off a nightlight on patient support apparatus 20; turning off power to a mattress 40 positioned on patient support apparatus 20; turning off power to one or more amplifiers on patient support apparatus 20 (e.g. amplifiers for a radio or for nurse-call communication) and/or other actions.

In some embodiments, any one or more of the actions automatically undertaken by controller 96 in response to detecting patient support apparatus 20 has exited a room are modified to be contingent upon whether or not a patient is present on patient support apparatus 20, as detected by patient presence detector 98. For example, if no patient is present when a patient support apparatus 20 is moved out of a room, then controller 96 is configured in some embodiments to skip automatically performing one or more of the following actions: sending a command to turn off a television or radio (or turn down the volume of the television or radio); sending a command to thermostat 66; sending a command to room lights 64; and/or other actions. Other changes may be implemented based on the presence or absence of a patient on patient support apparatus 20.

In addition to carrying out the room entry/exit detection functions described above, headwall interface 72 and first and second transceivers 90 and 92 are configured to carry out a plurality of additional functions. Some of these additional functions have been previously described and include the communication of voice signals between a patient supported on patient support apparatus 20 and a nurse positioned remotely at a nurse's station, the communication of control signals between patient support apparatus 20 and room interface board 58 (and the components in communication with room interface board 58), and the communication of data/alerts to nurse call system 60. Further, first and second transceivers 90 and 92 may carry out any of the functions disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference.

It will be understood that, although first and second transceivers 90 and 92 and controller 96 have been described herein as being integral to patient support apparatus 20, these component may be modified to be part of a separable module that is inserted into patient support apparatus 20. For example, in one such modified embodiment, transceivers 90 and 92 and controller 96 are packaged into a removable module, such as a dongle, that is inserted into a port on patient support apparatus 20. When so inserted, the module allows all of the aforementioned communication abilities and movement detection abilities to be carried out by the patient support apparatus 20. This enables conventional existing patient support apparatuses 20 to be converted to patient support apparatuses having the functionality described herein. In some embodiments, the port on patient support apparatus 20 that the module plugs into is the cable interface 94 of the patient support apparatus 20.

As previously noted, headwall interface 72 may be configured to send a "cord-out" alert to room interface board via cable interface 56 if either wired or wireless communication between itself and patient support apparatus 20 is unexpectedly lost. Room interface board 58 forwards this cord-out alert to nurse call system 60. In at least some of those embodiments of headwall interface 72 that are adapted to send such cord-out alerts, headwall interfaces 72 are adapted to eliminate such cord-out alerts when it detects that patient support apparatus 20 is exiting a room. Headwall interface 72 detects that patient support apparatus 20 is exiting the room in the same manner controller 96 detects this exit. That is, headwall interface 72 includes a controller that monitors the order in which communication links 116 and 118 are disestablished between headwall interface 72 and patient support apparatus 20. When the controller of headwall interface 72 determines that communication link 116 is first disestablished followed by communication link 118, it is configured in some embodiments to not issue a cord-out alert because it is presumed that the ordered disestablishment of communication links 116 and 118 is a result of the patient support apparatus 20 being moved out of the bay area and room, rather than the result of both of those communication links suffering an ordered malfunction.

Although not mentioned above, it will be understood that the establishment of communication links 116 and 118 between a patient support apparatus 20 and headwall interface 72 takes place automatically without requiring any steps on the part of a caregiver that are specific to this process. In other words, the caregiver does not need to press a button, flip a switch, or manipulate any controls on either patient support apparatus 20 or headwall interface 72. Instead, the mere positioning of patient support apparatus 20 within range of first and/or second wall units 68 and 70 automatically causes patient support apparatus 20 to establish communication links with these devices.

In those situations where a room contains multiple headwall interfaces 72, Bluetooth transceiver 92 may initially establish a communication link 118 with a headwall interface 72 when entering a room that is not the headwall interface in which the patient support apparatus 20 is ultimately parked in front of. In other words, when patient support apparatus 20 is initially moved into a room with multiple headwall interfaces 72, second transceiver 92 generally has enough range to be able to communicate with both (or all) of the headwall interfaces 72 within that room. Multiple communication links 118 may therefore be initially established. However, once the patient support apparatus 20 is moved to a specific bay area 114, the patient support apparatus 20 receives the unique identifier corresponding to the headwall interface 72 of that particular bay area 114. This is sent to patient support apparatus 20 via first transceiver 90. Controller 96 uses this specific identifier to determine that which of the multiple headwall interfaces 72 it is supposed to have second communication link 118 with. It therefore disestablishes any second communication links 118 it may have established with the other headwall interfaces 72 that do not have the specific identifier it received via first transceiver 90. The result is that patient support apparatus 20 ends up having a single communication link 116 and a single communication link 118 with only one (and the same) headwall interface 72.

In some embodiments, controller 96 is configured to utilize headwall interface map information stored on board patient support apparatus 20 in order to supplement the determination of whether or not patient support apparatus 20 is entering or exiting a room. This information is used in conjunction with the sequence in which second transceiver 92 comes into and out of communication ranges of the multiple headwall interfaces 72. For example, if a room contains a first headwall interface 72 close to the door of a room 112 and a second headwall interface 72 that is farther away from the door, controller 96 may use second transceiver 90's ability to communicate with the two headwall interfaces 72 to confirm entry or exit of patient support apparatus 20. This is done by monitoring the order in which second transceiver 92 comes into, or out of, communication range with the two headwall interface 72.

If second transceiver 92 first comes into communication range of the headwall interface 72 closer to the door and then into communication range of the headwall interface 72 farther from the door, this provides confirmation that the patient support apparatus has just entered the room, moved past the closer headwall interface, and is now positioned near the farther headwall interface 72. Conversely, if second transceiver 92 first disestablishes communication link 118 with the headwall interface 72 farther from the door, but still remains in communication range of the headwall interface 72 closer to the door for some time after moving out of range of the farther headwall interface 72, and then eventually loses communication with both headwall interfaces 72, this provides confirmation that patient support apparatus 20 has been moved out of the room 112. Controller 96 thus uses an on-board map of the locations of each of the headwall interfaces 72 along with the order in which communication link 118 is established/disestablished with the headwall interfaces 72 to determine how patient support apparatus 20 is moving throughout a healthcare facility. This information is used in addition to the monitoring of the order in which communication links 116 and 118 are established and disestablished relative to each other when determining if patient support apparatus 20 is entering or exiting a room.

In addition to any one or more of the methods or factors described above that are used by controller 96 to determine if patient support apparatus 20 is entering or exiting a room, controller 96 is also programmed in some embodiments to monitor the signal strengths of the communication links 116 and 118 when determining whether patient support apparatus 20 is entering or exiting a room. Controller 96 does this by determining whether signals strengths are abruptly changed or gradually changed in the moments before a communication link is disestablished or in the moments after a communication link is established. Where there is a gradual change (reduction) in signal strength in the moments before a communication link (116 or 118) is disestablished, this is indicative of the patient support apparatus 20 being moved away from the adjacent headwall interface 72. If there is an abrupt change in signal strength in the moments before the communication link is disestablished, this is indicative that the disestablishment of the communication link was due to interference, or some other factor other than the movement of the patient support apparatus 20.

Conversely, if there is a gradual change (increase) in signal strength in the moments after a communication link is established, this is indicative of patient support apparatus 20 moving closer to a headwall interface 72. However, if there is an abrupt change in signal strength in the moments after a communication link is established, this is indicative of an obstruction having been removed (or added), or some other cause unrelated to movement of patient support apparatus 20. As noted, these signal strength measurements may be used in conjunction with any or all of the other factors and methods described above when controller 96 determines whether patient support apparatus 20 is entering or exiting a room.

It will be understood that various modifications may be made to the structures and methods described herein. For example, although headwall unit 72 has been described as comprising first and second wall units 68 and 70, it will be understood that these wall units 68 and 70 do not need to be mounted to a wall. Instead, these units 68 and/or 70 can be mounted in any fixed location within a room, including, but not limited to, the ceiling, the floor, or to other architectural structures within the room. It will also be understood that controller 96 may be modified to communicate with nurse call system 60 via third transceiver 102 in addition to such communication via headwall interface 72. Communicating via third transceiver 102 can be useful in situations where patient support apparatus 20 has been moved out of a room and is no longer in communication with the headwall interface 72. By communicating using third transceiver 102, controller 96 is able to send a message to the nurse call system 60 (via access points 108) indicating that it has moved away from headwall interface 72, and the nurse call system 60 can therefore cancel any cord-out alert that may have existed and/or take other actions knowing that patient support apparatus 20 is no longer positioned at that particular headwall interface 72.

It will also be understood that the use of the term "transceiver" herein is intended to cover not only devices that include a transmitter and receiver contained within a single unit, but also devices having a transmitter separate from a receiver, and/or any other devices that are capable of both transmitting and receiving signals or messages.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room; and
a controller adapted to automatically determine from the first and second wireless communications when the patient support apparatus is leaving the room by monitoring an order in which the first and second transceivers discontinue communication with the first and second headwall units, respectively.

2. The patient support apparatus of claim 1 wherein the controller is further adapted to automatically determine when the patient support apparatus is entering the room, and the controller does so by monitoring an order in which the first and second transceivers establish communication with the first and second headwall units, respectively.

3. The patient support apparatus of claim 1 wherein the first transceiver is an infrared transceiver and the second transceiver is a radio frequency transceiver.

4. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room;
a controller adapted to automatically determine from the first and second wireless communications at least one of the following: (1) when the patient support apparatus is leaving the room, and (2) when the patient support apparatus is entering the room; and
wherein the first transceiver is adapted to communicate first periodic heartbeat messages with the first headwall unit, the second transceiver is adapted to communicate second periodic heartbeat messages with the second headwall unit, and the controller is adapted to forward information to a remote device indicative of successful communication of the first and second heartbeat messages.

5. The patient support apparatus of claim 4 wherein the patient support apparatus is a bed, the first transceiver is an infrared transceiver, and the second transceiver is a radio frequency transceiver.

6. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room;
a controller adapted to automatically determine from the first and second wireless communications at least one of the following: (1) when the patient support apparatus is leaving the room, and (2) when the patient support apparatus is entering the room;
a nurse call cable interface for connecting a nurse call cable between the patient support apparatus and a nurse call outlet of a nurse call system; and
a nurse call connection detector adapted to detect when the nurse call cable is in communication with the nurse call system;
wherein the controller is further adapted to alert a caregiver to couple the nurse call cable between the patient support apparatus and the nurse call outlet if the caregiver fails to do so and the first and second transceivers have established communication with the first and second headwall units, respectively.

7. The patient support apparatus of claim 6 wherein the patient support apparatus is a bed, the first transceiver is an infrared transceiver, and the second transceiver is a radio frequency transceiver.

8. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room; and
a controller adapted to automatically determine from the first and second wireless communications at least one of the following: (1) when the patient support apparatus is leaving the room, and (2) when the patient support apparatus is entering the room; and
a patient presence detector adapted to detect when a patient is present on the support surface and when a patient is not present on the support surface;
wherein the controller is further adapted to automatically deactivate at least one function of the patient support apparatus if the controller determines the patient support apparatus is leaving the room and the patient is not present on the support surface.

9. The patient support apparatus of claim 7 wherein the patient support apparatus is a bed, the first transceiver is an infrared transceiver, and the second transceiver is a radio frequency transceiver.

10. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room; and
a controller adapted to automatically determine from the first and second wireless communications at least one of the following: (1) when the patient support apparatus is leaving the room, and (2) when the patient support apparatus is entering the room; and wherein the controller is further adapted to send a message to a remote device in response to determining the patient support apparatus is leaving the room, the message including an instruction to perform at least one of the following: (1) turn off a room light; (2) turn off a radio; (3) turn off a television; and (4) change a temperature setting in the room.

11. A patient support apparatus comprising:
a support surface adapted to support a person;
a first transceiver adapted to establish first wireless communication with a first headwall unit positioned at a fixed location in a room;
a second transceiver adapted to establish second wireless communication with a second headwall unit positioned at a fixed location in the room; and
a controller adapted to automatically send a first message to a remote device indicating the patient support apparatus is not in the room if the first and second transceivers are unable to establish first and second wireless communication with the first and second headwall units, respectively; and wherein the controller is further adapted to send a second message to the remote device indicating the patient support apparatus is in a particular bay of the room if the first and second transceivers are able to establish first and second wireless communication with the first and second headwall units, respectively.

12. The patient support apparatus of claim 11 wherein the controller is further adapted to send a third message to the remote device indicating the patient support apparatus is in the room and an error condition exists if only one of the first and second transceivers is able to establish communication with the first and second headwall units, respectively.

13. The patient support apparatus of claim 11 wherein the first transceiver is an infrared transceiver and the second transceiver is a radio frequency transceiver.

14. The patient support apparatus of claim 13 wherein the controller is further adapted to automatically determine from the first and second wireless communications when the patient support apparatus is leaving the room, and the controller does so by monitoring an order in which the first and second transceivers discontinue communication with the first and second headwall units, respectively.

15. The patient support apparatus of claim 13 further comprising a patient presence detector adapted to detect when a patient is present on the support surface and when a patient is not present on the support surface; and wherein the controller is further adapted to automatically deactivate at least one function of the patient support apparatus if the controller determines the patient support apparatus is leaving the room and the patient is not present on the support surface.

16. The patient support apparatus of claim 13 wherein the controller automatically determines when the patient support apparatus is entering the room, and the controller does so by monitoring an order in which the first and second transceivers establish communication with the first and second headwall units, respectively; and wherein the controller is further adapted to send a message to a remote device in response to determining the patient support apparatus is entering the room, the message including an instruction to perform at least one of the following: (1) turn on a room light; (2) turn on a radio; (3) turn on a television; (4) change a temperature setting in the room; and (5) alert a caregiver to couple a power cable between the patient support apparatus and an electrical outlet.

17. A patient support apparatus comprising:
a support surface adapted to support a person;
a movement detector adapted to detect if the patient support apparatus is moving into or out of a room, the movement detector comprising:
(a) a first transceiver adapted to establish first wireless communication with a first headwall unit positioned at a fixed location in a room; and
(b) a second transceiver adapted to establish second wireless communication with a second headwall unit positioned at a fixed location in the room; and
a controller adapted to automatically perform a first action if the movement detector detects the patient support apparatus is moving out of the room and to automatically perform a second action if the movement detector detects the patient support apparatus is moving into the room;
wherein the first action is sending an instruction to perform at least one of the following: (1) turn off a room light; (2) turn off a radio; (3) turn off a television; and (4) change a temperature setting in the room; and wherein the second action is sending an instruction to perform at least one of the following: (1) turn on a room light; (2) turn on a radio; (3) turn on a television; (4) change a temperature setting in the room; and (5) alert a caregiver to couple a power cable between the patient support apparatus and an electrical outlet.

18. A patient support apparatus comprising:
a support surface adapted to support a person;
a movement detector adapted to detect if the patient support apparatus is moving into or out of a room, the movement detector comprising:
(a) a first transceiver adapted to establish first wireless communication with a first headwall unit positioned at a fixed location in a room; and
(b) a second transceiver adapted to establish second wireless communication with a second headwall unit positioned at a fixed location in the room;
a controller adapted to automatically perform a first action if the movement detector detects the patient support apparatus is moving out of the room and to automatically perform a second action if the movement detector detects the patient support apparatus is moving into the room; and
a patient presence detector adapted to detect when a patient is present on the support surface and when a patient is not present on the support surface, and wherein the controller chooses the second action based upon whether the patient is present or not, and the controller chooses the first action based upon whether the patient is present or not.

19. A patient support apparatus comprising:

a support surface adapted to support a person;

a movement detector adapted to detect if the patient support apparatus is moving into or out of a room, the movement detector comprising:
   (a) a first transceiver adapted to establish first wireless communication with a first headwall unit positioned at a fixed location in a room; and
   (b) a second transceiver adapted to establish second wireless communication with a second headwall unit positioned at a fixed location in the room; and a controller adapted to automatically perform a first action if the movement detector detects the patient support apparatus is moving out of the room and to automatically perform a second action if the movement detector detects the patient support apparatus is moving into the room.

20. The patient support apparatus of claim 19 wherein the controller determines the patient support apparatus is leaving the room by monitoring an order in which the first and second transceivers discontinue communication with the first and second headwall units, respectively; and wherein the controller determines the patient support apparatus is entering the room by monitoring the order in which the first and second transceivers establish communication with the first and second headwall units, respectively.

* * * * *